United States Patent
Hu

(10) Patent No.: US 9,933,416 B1
(45) Date of Patent: Apr. 3, 2018

(54) DETECTION AND QUANTIFICATION OF POLYPEPTIDES IN PLANTS WITHOUT A REFERENCE STANDARD BY MASS SPECTROMETRY

(71) Applicant: PIONEER HI-BRED INTERNATIONAL INC, Johnston, IA (US)

(72) Inventor: Xuehua Hu, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 781 days.

(21) Appl. No.: 14/340,135

(22) Filed: Jul. 24, 2014

Related U.S. Application Data

(60) Provisional application No. 61/859,853, filed on Jul. 30, 2013.

(51) Int. Cl.
| | |
|---|---|
| *G01N 33/48* | (2006.01) |
| *G01N 33/50* | (2006.01) |
| *H01J 49/00* | (2006.01) |
| *G01N 30/72* | (2006.01) |
| *G01N 30/02* | (2006.01) |
| *G01N 33/02* | (2006.01) |
| *G01N 33/68* | (2006.01) |
| *G01N 33/00* | (2006.01) |

(52) U.S. Cl.
CPC ..... *G01N 33/5097* (2013.01); *G01N 30/7233* (2013.01); *H01J 49/004* (2013.01); *H01J 49/0027* (2013.01); *G01N 33/0098* (2013.01); *G01N 33/025* (2013.01); *G01N 33/6848* (2013.01); *G01N 2030/027* (2013.01)

(58) Field of Classification Search
CPC .. G01N 33/0098; G01N 33/02; G01N 33/025; G01N 33/5097; G01N 33/6848
See application file for complete search history.

(56) References Cited

U.S. PATENT DOCUMENTS

| | | |
|---|---|---|
| 7,070,949 B2 | 7/2006 | Suckau et al. |
| 7,422,865 B2 | 9/2008 | Fischer |
| 7,635,573 B2 | 12/2009 | Fischer |
| 7,851,742 B2 | 12/2010 | Geromanos et al. |
| 7,910,372 B2 | 3/2011 | Ishihama |
| 8,187,893 B2 | 5/2012 | Hunter |
| 8,193,485 B2 | 6/2012 | Geromanos et al. |
| 8,227,252 B2 | 7/2012 | Lawry et al. |
| 8,271,203 B2 | 9/2012 | Hunter et al. |
| 8,373,115 B2 | 2/2013 | Geromanos et al. |
| 8,633,031 B2 | 1/2014 | Hunter |
| 2006/0078960 A1 | 4/2006 | Hunter |
| 2008/0206737 A1 | 8/2008 | Hunter |

FOREIGN PATENT DOCUMENTS

| | | |
|---|---|---|
| WO | 2004/090552 A1 | 10/2004 |
| WO | 2010/035504 A1 | 4/2010 |

OTHER PUBLICATIONS

Hu, X. Tiger et al. "Multiplexed protein quantification in maize leaves by liquid chromatography coupled with tandem mass spectrometry: an alternative tool to immunoassays for target protein analysis in genetically engineered crops." J. Agricultural and Food Chemistry (2011) 59 3551-3558.*
Zhang, Junmei et al. "MS/MS/MS reveals false positive identification of histone serine methylation." J. Proteome Res. (2010) 9 585-594.*
Herman, Eliot M. et al. "Genetic modification removes an immunodominant allergen from soybean." Plant Physiology (2003) 132 36-43. (Year: 2003).*
Anderson, et al. "Quantitative Mass Spectrometric Multiple Reaction Monitoring Assays for Major Plasma Proteins", Molecular and Cellular Proteomics_2006_Vol5_573-588.
Champion, et al. "Targeted, Hypothesis-Driven Mass Spectrometry: MRM Initiated Detection and Sequencing using the MIDAS Workflow for Faster, More Intelligent and Sensitive Protein Discovery and Characterization", Applied Biosystems—Technical Note.
Fiehn, et al. Encyclopedia Reference of Genomics & Proteomics in Molecular Medicine_2006_pt13_US Davis Genome Center_pp. 1030-1034.
Lenz, et al. Applied BioSystems Technical Note_Validation of Identifications of Low Abundance Proteins using the MIDAS on a 4000 Q Trap LC/MS System Workflow.
Unwin, et al. A Sensitive Mass Spectrometric Method for Hypothesis-Driven Detection of Peptide Post-Translational Modifications: Multiple Reaction Monitoring-Initiated Detection and Sequencing (MIDAS)_Nature Publishing Group_2009_vol4_No6_870-877.
Unwin, et al. "Multiple Reaction Monitoring to Identify Sites of Protein Phosphorylation with High Sensitivity" _Molecular & Cellular Proteomics_2005_Vol4_1134-1144.
Vissers_"Analysis and Quantification of Diagnostic Serum Markers and Protein Signatures for Gaucher Disease" Molecular & Cellular Proteomics_2007_Vol6_755-766.
Wang, et al. "Quantification of Proteins and Metabolites by Mass Spectrometry Without Isotopic Labeling or Spiked Standards" Anal. Chem_2003_Vol75_4818-4826.
Wienkoop, et al. "Cell-specific Protein Profiling in Arabidopsis Thaliana Trichomes: Identification of Trichome-located Proteins Involved in Sulfur Metabolism and Detoxification", Phytochemistry_65_2004_1641-1649.

(Continued)

*Primary Examiner* — Christopher Adam Hixson
(74) *Attorney, Agent, or Firm* — Pioneer Hi-Bred Int'l, Inc.

(57) ABSTRACT

A method is provided for detecting a polypeptide of interest in a plant without the use of a reference standard. The method comprises the steps of obtaining a plant expressing the polypeptide of interest and a negative control plant that does not express the polypeptide of interest, and analyzing a sample from each in an information-dependent acquisition (IDA) method. A method is also provided for determining the relative expression level of a polypeptide of interest in a plurality of plants without the use of a reference standard. This method comprises the steps of obtaining a plurality of plants expressing the polypeptide of interest and a negative control plant that does not express the polypeptide of interest, analyzing samples from each in an IDA method, and determining the relative expression level of the polypeptide in each of the plurality of plants.

16 Claims, 6 Drawing Sheets

(56) References Cited

OTHER PUBLICATIONS

Figure 1A:
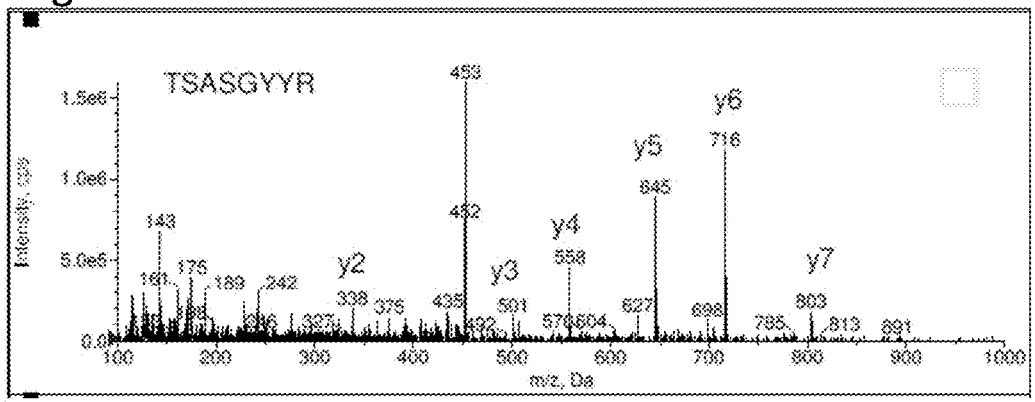

Wienkoop, et al. "Relative and Absolute Quantitative Shotgun Proteomics: Targeting Low-Abundance Proteins in Arabidobsis Thaliana", Journal Experimental Botany_2006_Vol57_1529-1535.
Wienkoop, et al. "Absolute quantification of Medicago Truncatula Sucrose Synthase Isoforms and N-Metabolism Enzymes in Symbiotic Root Nodules and the Detection of Novel Nodule Phosphoproteins by Mass Spectrometry", JournalExperimentalBotany_2008_Vol59_No12_3307-3315.

* cited by examiner

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial sequence
<220> FEATURE:
<223> OTHER INFORMATION: From variant GAT polypeptide produced by
      gene-shuffling

<400> SEQUENCE: 1

Thr Ser Ala Ser Gly Tyr Tyr Arg
1               5

<210> SEQ ID NO 2
<211> LENGTH: 9
<212> TYPE: PRT
<213> ORGANISM: Artificial sequence
<220> FEATURE:
<223> OTHER INFORMATION: From variant GAT polypeptide produced by
      gene-shuffling

<400> SEQUENCE: 2

Gly Val Ala Thr Leu Glu Gly Tyr Arg
1               5

<210> SEQ ID NO 3
<211> LENGTH: 7
<212> TYPE: PRT
```

```
<213> ORGANISM: Artificial Sequence
<220> FEATURE:
<223> OTHER INFORMATION: From variant GAT polypeptide produced by
      gene-shuffling

<400> SEQUENCE: 3

His Ala Glu Glu Ile Leu Arg
1               5

<210> SEQ ID NO 4
<211> LENGTH: 10
<212> TYPE: PRT
<213> ORGANISM: Streptomyces hygroscopicus

<400> SEQUENCE: 4

Leu His Glu Ala Leu Gly Tyr Thr Ala Arg
1               5                   10

<210> SEQ ID NO 5
<211> LENGTH: 12
<212> TYPE: PRT
<213> ORGANISM: Bacillus thuringiensis

<400> SEQUENCE: 5

Ser Ala Thr Pro Thr Asn Thr Ile Asp Pro Glu Arg
1               5                   10

<210> SEQ ID NO 6
<211> LENGTH: 10
<212> TYPE: PRT
<213> ORGANISM: Bacillus thuringiensis

<400> SEQUENCE: 6

Thr Gly His Thr Leu Gln Leu Glu Asp Lys
1               5                   10

<210> SEQ ID NO 7
<211> LENGTH: 14
<212> TYPE: PRT
<213> ORGANISM: Bacillus thuringiensis

<400> SEQUENCE: 7

Val Leu Thr Ala Gly Thr Gly Gln Ala Leu Gly Leu Ile Arg
1               5                   10
```

DETECTION AND QUANTIFICATION OF POLYPEPTIDES IN PLANTS WITHOUT A REFERENCE STANDARD BY MASS SPECTROMETRY

CROSS-REFERENCE TO RELATED APPLICATIONS

This application claims priority to and the benefit of U.S. Provisional Patent Application Ser. No. 61/859,853, filed on Jul. 30, 2013, which is hereby incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named "4262USNP_ST25.txt" created on Jul. 8, 2014, and having a size of 4 kilobytes and is filed concurrently with the specification. The sequence listing contained in this ASCII formatted document is part of the specification and is herein incorporated by reference in its entirety.

FIELD OF THE INVENTION

The invention relates to the field of mass spectrometry. Specifically, the invention provides methods for the detection and quantification of polypeptides in plants without the use of a reference standard.

BACKGROUND OF THE INVENTION

Immunoassays, such as Western blots and Enzyme Linked Immunosorbent Assays (ELISAs), have long been the primary method for target protein detection and quantification in biological samples, including transgenic crops. ELISAs have remained a popular choice because of their throughput, sensitivity, and selectivity. The drawback to ELISAs and other immunoassays is the need for high quality antibodies that may not be readily available and the significant time (approximately 10-20 months) and resources needed to develop an assay. Additionally, a separate assay is typically needed for each protein of interest. Multiplexed methods are desirable as genetically engineered crops featuring stacked traits/proteins become more prevalent.

Mass spectrometry has become an important tool for targeted protein detection and quantification. The first fully validated liquid chromatography coupled with tandem mass spectrometry (LC-MS/MS) method for the detection and quantification of multiple target proteins in transgenic maize was recently reported. In that study, transgenic sample extracts, along with calibration curves made by spiking recombinant proteins into null (non-transgenic) tissue extract, were efficiently digested with the protease trypsin. Signature peptides were detected and quantified by multiple reaction monitoring (MRM) as protein surrogates. In a similar manner, liquid chromatography coupled with multiple reaction monitoring (LC-MRM) was used to quantify a *Bacillus thuringiensis* (Bt) protein, Cry1Ab, in transgenic maize leaves. In both cases, protein reference standards were required. Therefore, methods are needed for detecting and quantifying polypeptides in a plant without the use of a reference standard.

BRIEF SUMMARY OF THE INVENTION

A method is provided for detecting at least one polypeptide of interest in a plant or a plurality of plants without the use of a reference standard. The method comprises the steps of obtaining a first sample from one or more plants expressing the polypeptide of interest and obtaining a second sample from at least one negative control plant that does not express the polypeptide of interest. Analysis is performed according to an information-dependent acquisition (IDA) method using liquid chromatography-tandem mass spectrometry (LC-MS/MS) and databases to detect and identify tryptic peptides derived from the polypeptide of interest in the sample. The method then determines whether the polypeptide of interest is present in the plant or plants by using retention times obtained by the IDA method and comparing chromatograms of the first sample and the second sample. The method can further be used to determine the relative expression level of the polypeptide of interest. In this manner, the chromatogram peaks associated with the polypeptide of interest are integrated and the relative expression level of the polypeptide of interest is determined in each plant, wherein a higher relative expression level is indicated by a larger integrated peak value.

The method can further comprise the step of selecting one or more plants having a higher relative expression level of the polypeptide of interest. Such plants can be used in breeding programs.

The following embodiments are encompassed by the present invention:

1. A method of detecting a polypeptide of interest in a plant without the use of a reference standard, said method comprising:
   (a) obtaining a plant expressing said polypeptide of interest and a negative control plant that does not express said polypeptide of interest;
   (b) preparing a sample from said plant and a negative control sample from said negative control plant for analysis, wherein said sample and said negative control sample are subjected to trypsin digestion;
   (c) performing an information-dependent acquisition (IDA) method on said sample using liquid chromatography-tandem mass spectrometry (LC-MS/MS), said IDA method comprising:
      (i) predicting all tryptic peptides that can be derived from said polypeptide of interest and predicting the multiple reaction monitoring (MRM) transitions for each of said tryptic peptides;
      (ii) performing a survey scan of said sample using LC-MS/MS to monitor for the predicted MRM transitions of said tryptic peptides, wherein tandem mass spectrometry is performed in MRM mode, and wherein LC-MRM ion chromatograms are produced for said sample;
      (iii) performing an IDA scan when an individual MRM transition signal exceeds a predetermined threshold, wherein said IDA scan is an enhanced product ion (EPI) scan that is performed using tandem mass spectrometry in linear ion trap mode, and wherein said EPI scan produces a set of MS/MS spectra for said tryptic peptide associated with said MRM transition signal; and
      (iv) identifying said tryptic peptide associated with said MRM transition signal, and determining the retention time of said MRM transition signal in said LC-MRM ion chromatograms, by submitting said set of MS/MS spectra to at least one database;
   (d) repeating said IDA method of step (c) with said negative control sample; and (e) determining whether an MRM transition signal is present at said determined retention time in said LC-MRM ion chromatograms of said sample and said negative control sample;

wherein the presence of an MRM transition signal at said determined retention time in said sample, and the absence of a corresponding MRM transition signal in said negative control sample, indicates the presence of said polypeptide of interest in said plant.

2. The method of embodiment 1, further comprising the steps of:
   (a) producing a synthetic peptide comprising the amino acid sequence of said tryptic peptide associated with said MRM transition signal;
   (b) preparing a synthetic peptide sample from said synthetic peptide for analysis;
   (c) predicting the MRM transitions for said synthetic peptide;
   (d) performing steps (ii) through (iv) of said IDA method of embodiment 1 with said synthetic peptide sample; and
   (e) comparing said LC-MRM ion chromatograms of said sample, said negative control sample, and said synthetic peptide sample at said determined retention time; wherein the presence of an MRM transition signal at said determined retention time in said sample and said synthetic peptide sample, and the absence of a corresponding MRM transition signal in said negative control sample, confirms the presence of said polypeptide of interest in said plant.

3. The method of embodiment 1, further comprising the steps of:
   (a) producing a recombinant polypeptide comprising the amino acid sequence of said polypeptide of interest;
   (b) preparing a recombinant polypeptide sample from said recombinant polypeptide for analysis, wherein said recombinant polypeptide sample is subjected to trypsin digestion;
   (c) performing said IDA method of embodiment 1 with said recombinant polypeptide sample; and
   (d) comparing said LC-MRM ion chromatograms of said sample, said negative control sample, and said recombinant polypeptide sample at said determined retention time;

wherein the presence of an MRM transition signal at said determined retention time in said sample and said recombinant polypeptide sample, and the absence of a corresponding MRM transition signal in said negative control sample, confirms the presence of said polypeptide of interest in said plant.

4. The method of any one of the previous embodiments, wherein said method is used to detect two or more polypeptides of interest simultaneously in said plant.

5. The method of any one of the previous embodiments, wherein said predicted tryptic peptides have a length of 1 to 30 amino acids or a length of 6 to 20 amino acids.

6. The method of any one of the previous embodiments, wherein said predicted tryptic peptides are within the Q1 range of 300 to 1200 m/z or the Q1 range of 350 to 900 m/z.

7. The method of any one of the previous embodiments, wherein a maximum of 50 MRM transitions are detected by said IDA method.

8. The method of any one of the previous embodiments, wherein said predetermined threshold to perform said IDA scan is significantly higher than background noise.

9. The method of any one of the previous embodiments, wherein said IDA method is performed using a hybrid triple quadrupole mass spectrometer.

10. The method of any one of the previous embodiments, wherein said polypeptide of interest is a transgenic polypeptide.

11. The method of any one of the previous embodiments, wherein said plant is a transgenic plant.

12. The method of any one of the previous embodiments, wherein said negative control plant is a non-transgenic plant.

13. The method of any one of the previous embodiments, wherein said negative control plant is a transgenic plant that does not express said polypeptide of interest.

14. The method of any one of the previous embodiments, wherein said plant and said negative control plant are monocots.

15. The method of embodiment 14, wherein said monocots are maize, sugarcane, wheat, rice, barley, sorghum, or rye.

16. The method of any one of embodiments 1-13, wherein said plant and said negative control plant are dicots.

17. The method of embodiment 16, wherein said dicots are soybean, *Brassica*, sunflower, cotton, or alfalfa.

18. A method of determining the relative expression level of a polypeptide of interest in a plurality of plants without the use of a reference standard, said method comprising:
   (a) obtaining a plurality of plants expressing said polypeptide of interest and a negative control plant that does not express said polypeptide of interest;
   (b) preparing a first sample from a first plant, a second sample from a second plant, and a negative control sample from said negative control plant, wherein said first sample, said second sample, and said negative control sample are subjected to trypsin digestion;
   (c) performing an IDA method on said first sample using LC-MS/MS, said IDA method comprising:
      (i) predicting all tryptic peptides that can be derived from said polypeptide of interest and predicting the MRM transitions for each of said tryptic peptides;
      (ii) performing a survey scan of said first sample using LC-MS/MS to monitor for the predicted MRM transitions of said tryptic peptides, wherein tandem mass spectrometry is performed in MRM mode, and wherein LC-MRM ion chromatograms are produced for said first sample;
      (iii) performing an IDA scan when an individual MRM transition signal exceeds a predetermined threshold, wherein said IDA scan is an EPI scan that is performed using tandem mass spectrometry in linear ion trap mode, and wherein said EPI scan produces a set of MS/MS spectra for said tryptic peptide associated with said MRM transition signal; and
      (iv) identifying said tryptic peptide associated with said MRM transition signal, and determining the retention time of said MRM transition signal in said LC-MRM ion chromatograms, by submitting said set of MS/MS spectra to at least one database;
   (d) repeating said IDA method of step (c) with said second sample and said negative control sample;
   (e) determining whether an MRM transition signal is present at said determined retention time in said LC-MRM ion chromatograms of said first sample, said second sample, and said negative control sample, wherein the presence of an MRM transition signal at said determined retention time in said first sample and said second sample, and the absence of a corresponding MRM transition signal in said negative control sample, indicates the presence of said polypeptide of interest in said plurality of plants;

(f) integrating the peaks associated with said MRM transition signals in said LC-MRM ion chromatograms of said first sample and said second sample; and (g) determining the relative expression level of said polypeptide of interest in said first plant and said second plant, wherein a higher relative expression level is indicated by a larger integrated peak value.

19. The method of embodiment 18, further comprising the steps of:

(a) producing a synthetic peptide comprising the amino acid sequence of said tryptic peptide associated with said MRM transition signal;

(b) preparing a synthetic peptide sample from said synthetic peptide for analysis;

(c) predicting the MRM transitions for said synthetic peptide;

(d) performing steps (ii) through (iv) of said IDA method of embodiment 18 with said synthetic peptide sample; and (e) comparing said LC-MRM ion chromatograms of said first sample, said second sample, said negative control sample, and said synthetic peptide sample at said determined retention time;

wherein the presence of an MRM transition signal at said determined retention time in said first sample, said second sample, and said synthetic peptide sample, and the absence of a corresponding MRM transition signal in said negative control sample, confirms the presence of said polypeptide of interest in said plurality of plants.

20. The method of embodiment 18, further comprising the steps of:

(a) producing a recombinant polypeptide comprising the amino acid sequence of said polypeptide of interest;

(b) preparing a recombinant polypeptide sample from said recombinant polypeptide for analysis, wherein said recombinant polypeptide sample is subjected to trypsin digestion;

(c) performing said IDA method of embodiment 18 with said recombinant polypeptide sample; and (d) comparing said LC-MRM ion chromatograms of said first sample, said second sample, said negative control sample, and said recombinant polypeptide sample at said determined retention time;

wherein the presence of an MRM transition signal at said determined retention time in said first sample, said second sample, and said recombinant polypeptide sample, and the absence of a corresponding MRM transition signal in said negative control, confirms the presence of said polypeptide of interest in said plurality of plants.

21. The method of any one of embodiments 18 to 20, wherein the relative expression level of said polypeptide of interest is determined in more than two plants.

22. The method of any one of embodiments 18 to 21, said method further comprising the step of selecting a plant having a higher relative expression level of said polypeptide of interest.

23. The method of any one of embodiments 18 to 22, wherein said method is used to detect two or more polypeptides of interest simultaneously in said plurality of plants.

24. The method of any one of embodiments 18 to 23, wherein said predicted tryptic peptides have a length of 1 to 30 amino acids or a length of 6 to 20 amino acids.

25. The method of any one of embodiments 18 to 24, wherein said predicted tryptic peptides are within the Q1 range of 300 to 1200 m/z or the Q1 range of 350 to 900 m/z.

26. The method of any one of embodiments 18 to 25, wherein a maximum of 50 MRM transitions are detected by said IDA method.

27. The method of any one of embodiments 18 to 26, wherein said predetermined threshold to perform said IDA scan is significantly higher than background noise.

28. The method of any one of embodiments 18 to 27, wherein said IDA method is performed using a hybrid triple quadrupole mass spectrometer.

29. The method of any one of embodiments 18 to 28, wherein said polypeptide of interest is a transgenic polypeptide.

30. The method of any one of embodiments 18 to 29, wherein said plurality of plants are transgenic plants.

31. The method of any one of embodiments 18 to 30, wherein said negative control plant is a non-transgenic plant.

32. The method of any one of embodiments 18 to 30, wherein said negative control plant is a transgenic plant that does not express said polypeptide of interest.

33. The method of any one of embodiments 18 to 32, wherein said plurality of plants and said negative control plant are monocots.

34. The method of embodiment 33, wherein said monocots are maize, sugarcane, wheat, rice, barley, sorghum, or rye.

35. The method of any one of embodiments 18 to 32, wherein said plurality of plants and said negative control plant are dicots.

36. The method of embodiment 35, wherein said dicots are soybean, *Brassica*, sunflower, cotton, or alfalfa.

BRIEF DESCRIPTION OF THE SEVERAL VIEWS OF THE DRAWING(S)

The invention can be more fully understood from the following detailed description and the accompanying drawings and Sequence Listing, each of which form a part of this application.

FIG. 1A sets forth MS/MS spectra and y fragment ions of the TSASGYYR peptide (SEQ ID NO: 1), $[M+2H]^{2+}$ at m/z 452.707, derived from the GAT4621 polypeptide.

Figure 1B:
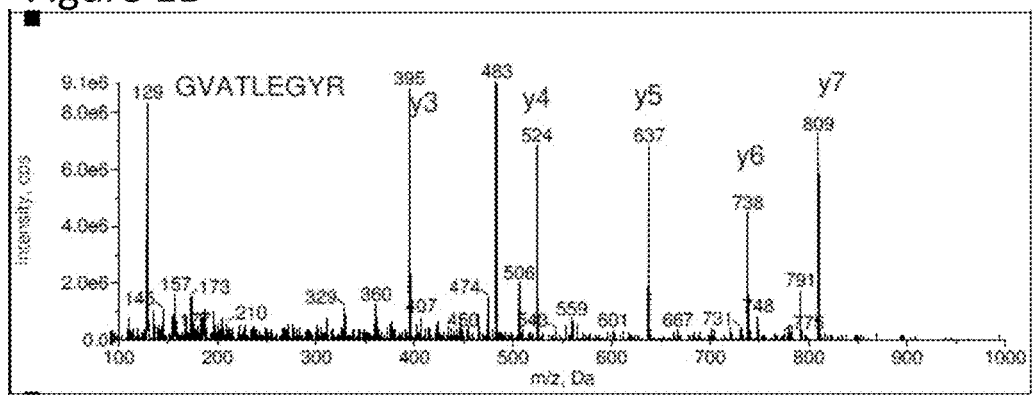

FIG. 1B sets forth MS/MS spectra and y fragment ions of the GVATLEGYR peptide (SEQ ID NO: 2), $[M+2H]^{2+}$ at m/z 483.252, derived from the GAT4621 polypeptide.

Figure 1C:
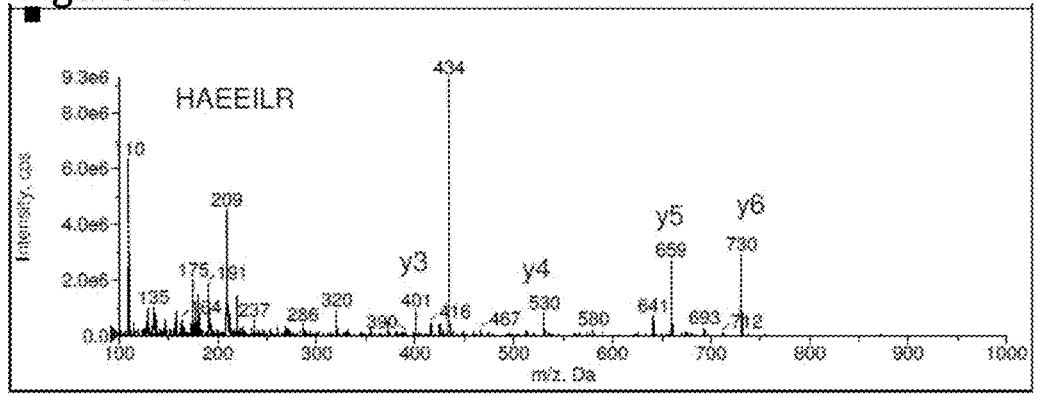

FIG. 1C sets forth MS/MS spectra and y fragment ions of the HAEEILR peptide (SEQ ID NO: 3), $[M+2H]^{2+}$ at m/z 434.233, derived from the GAT4621 polypeptide.

Figure 2A:
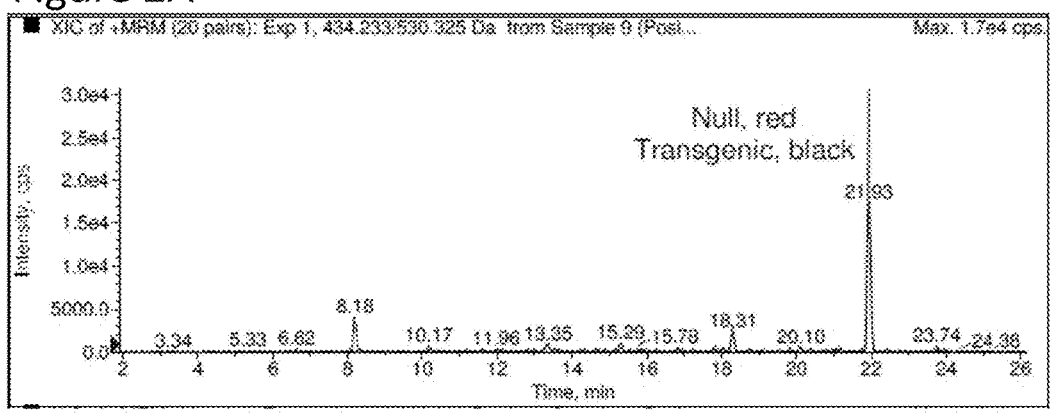

FIG. 2A sets forth overlays of LC-MRM ion chromatograms for transgenic plants (black), expressing a transgenic GAT4621 polypeptide, and null plants (red) that do not express the GAT4621 polypeptide. The product ion 530.3 m/z is shown for the peptide HAEEILR (SEQ ID NO: 3), $[M+2H]^{2+}$ at m/z 434.233.

Figure 2B:
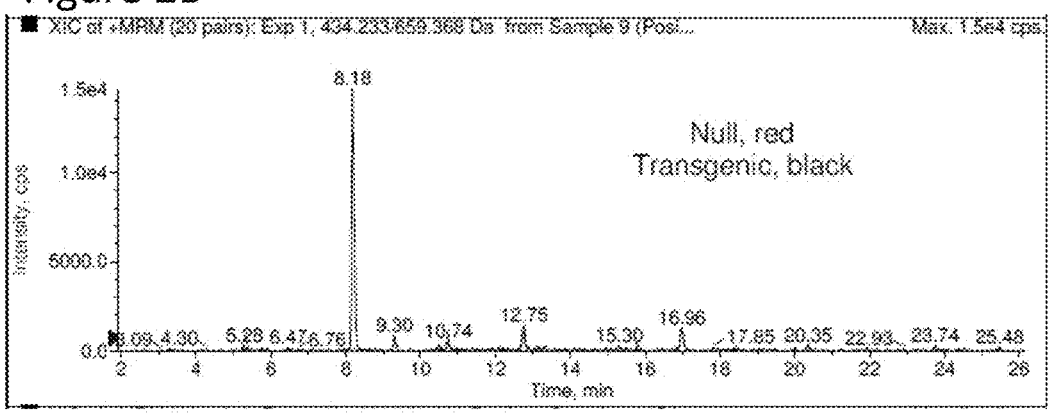

FIG. 2B sets forth overlays of LC-MRM ion chromatograms for transgenic plants (black), expressing a transgenic GAT4621 polypeptide, and null plants (red) that do not express the GAT4621 polypeptide. The product ion 659.4 m/z is shown for the peptide HAEEILR (SEQ ID NO: 3), $[M+2H]^{2+}$ at m/z 434.233.

Figure 2C:
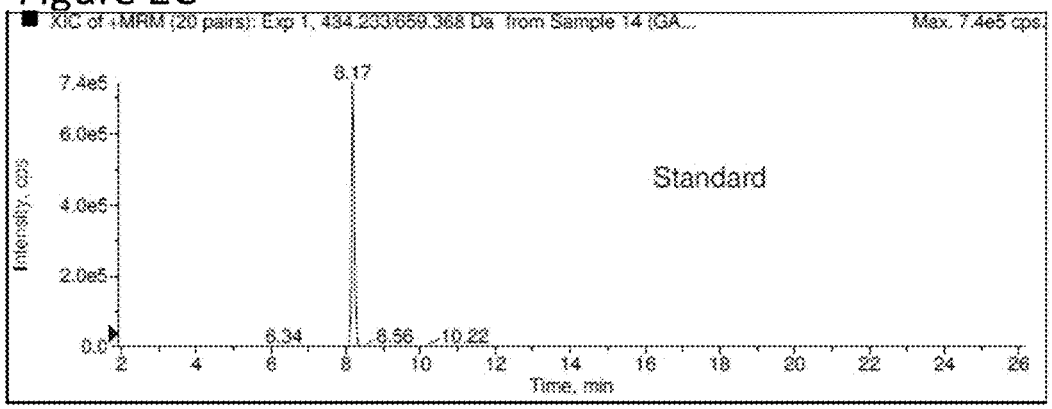

FIG. 2C sets forth an LC-MRM ion chromatogram of a standard polypeptide derived from the GAT4621 polypeptide. The LC-MRM ion chromatogram of 434.2/659.4 is shown for the digested GAT4621 standard.

Figure 3A:
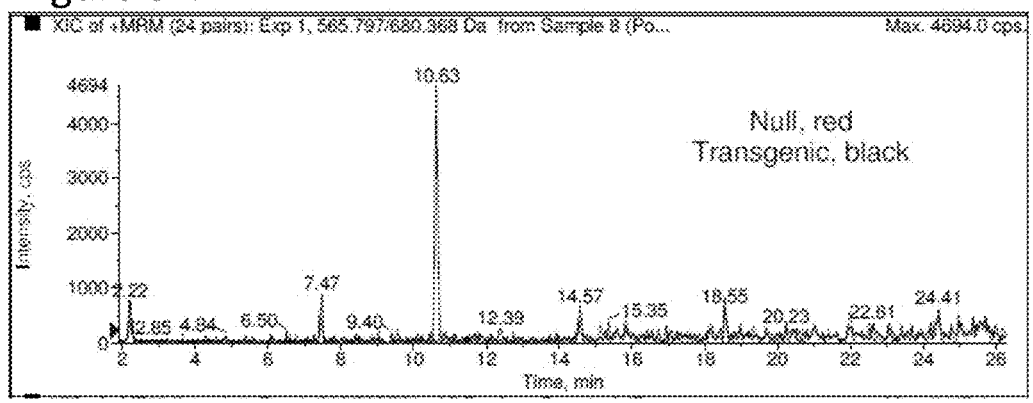

FIG. 3A sets forth overlays of LC-MRM ion chromatograms for transgenic plants (black), expressing a transgenic PAT polypeptide, and null plants (red) that do not express the PAT polypeptide. The product ion 680.4 m/z is shown for peptide LHEALGYTAR (SEQ ID NO: 4), $[M+2H]^{2+}$ at m/z 565.8.

Figure 3B:
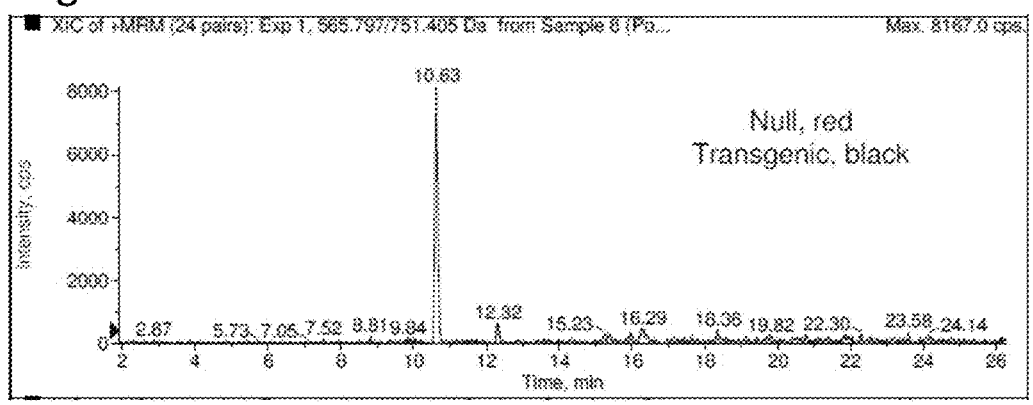

FIG. 3B sets forth overlays of LC-MRM ion chromatograms for transgenic plants (black), expressing a transgenic PAT polypeptide, and null plants (red) that do not express the PAT polypeptide. The product ion 751.4 m/z is shown for peptide LHEALGYTAR (SEQ ID NO: 4), $[M+2H]^{2+}$ at m/z 565.8.

Figure 3C:
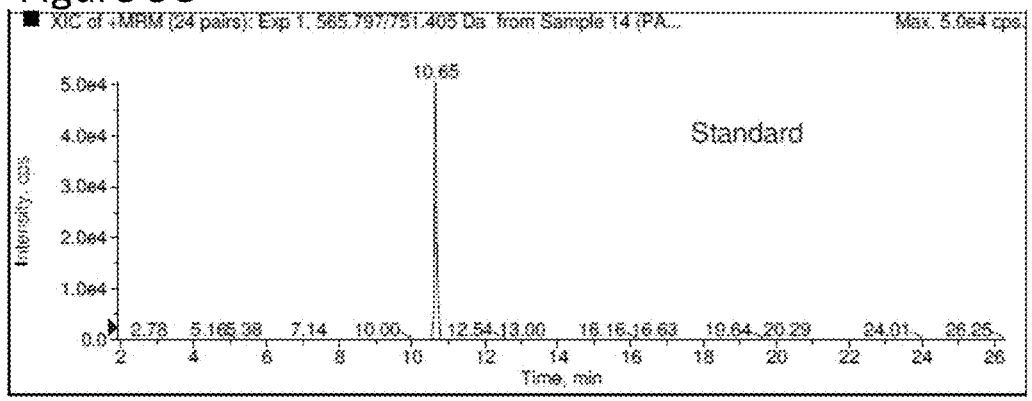

FIG. 3C sets forth an LC-MRM ion chromatogram of a standard polypeptide derived from the PAT polypeptide. The LC-MRM ion chromatogram of 565.8/751.4 is shown for the digested PAT standard.

Figure 4A:
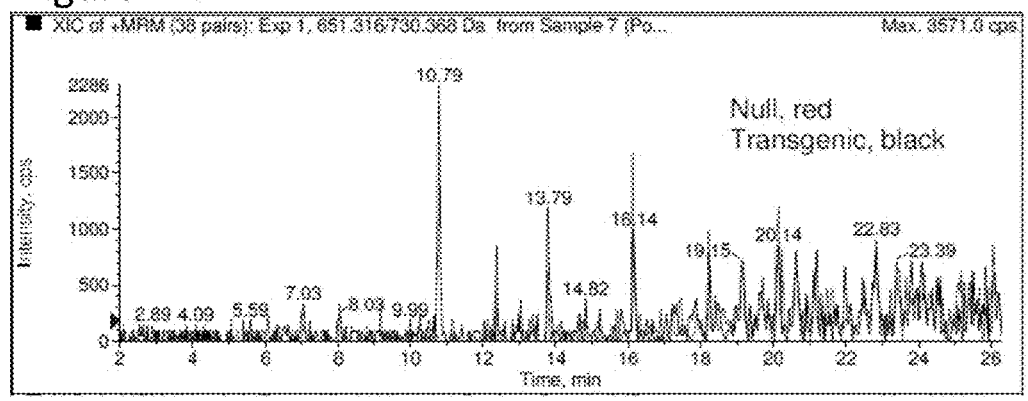

FIG. 4A sets forth overlays of LC-MRM ion chromatograms for transgenic plants (black), expressing a transgenic Cry1F polypeptide, and null plants (red) that do not express the Cry1F polypeptide. The product ion 730.4 m/z is shown for peptide SATPTNTIDPER (SEQ ID NO: 5), $[M+2H]^{2+}$ at m/z 651.3.

Figure 4B:
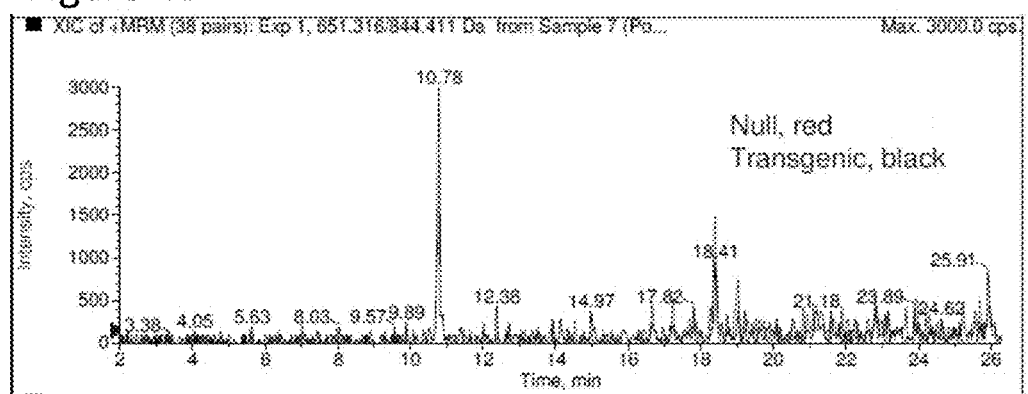

FIG. 4B sets forth overlays of LC-MRM ion chromatograms for transgenic plants (black), expressing a transgenic Cry1F polypeptide, and null plants (red) that do not express the Cry1F polypeptide. The product ion 844.4 m/z is shown for peptide SATPTNTIDPER (SEQ ID NO: 5), $[M+2H]^{2+}$ at m/z 651.3.

Figure 4C:
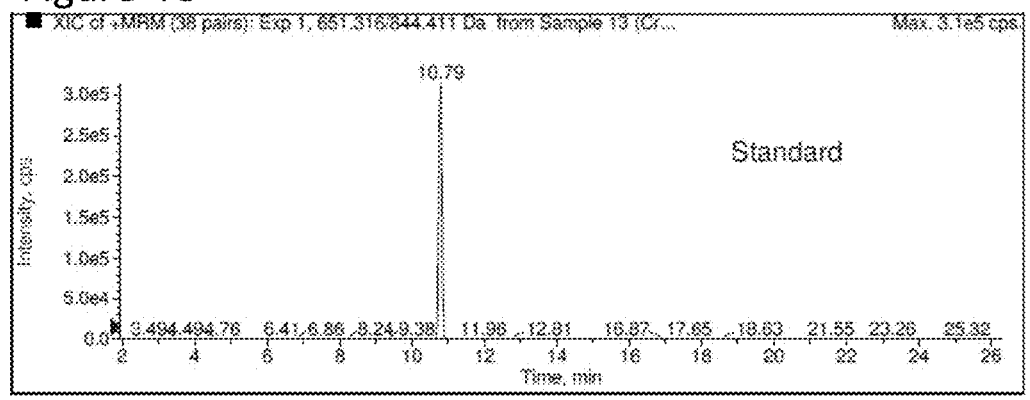

FIG. 4C sets forth an LC-MRM ion chromatogram of a standard polypeptide derived from the Cry1F polypeptide. The LC-MRM ion chromatogram of 651.3/844.4 is shown for the digested Cry1F standard.

Figure 5A:
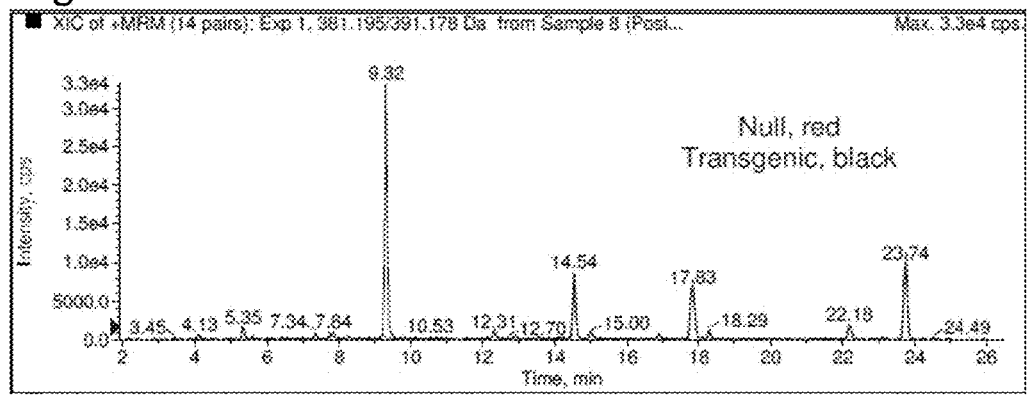

FIG. 5A sets forth overlays of LC-MRM ion chromatograms for transgenic plants (black), expressing a transgenic Cry34Ab1 polypeptide, and null plants (red) that do not express the Cry34Ab1 polypeptide. The product ion 391.2 m/z is shown for peptide TGHTLQLEDK (SEQ ID NO: 6), $[M+3H]^{3+}$ at m/z 381.2.

Figure 5B:
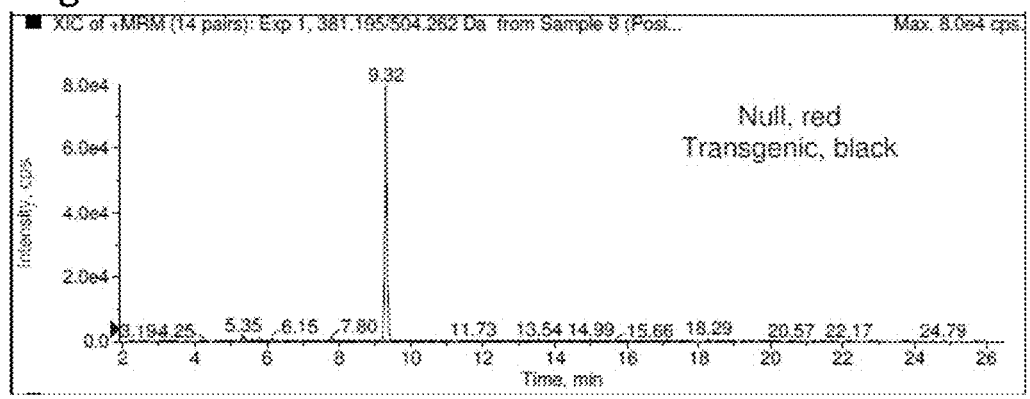

FIG. 5B sets forth overlays of LC-MRM ion chromatograms for transgenic plants (black), expressing a transgenic Cry34Ab1 polypeptide, and null plants (red) that do not express the Cry34Ab1 polypeptide. The product ion 504.3 m/z is shown for peptide TGHTLQLEDK (SEQ ID NO: 6), $[M+3H]^{3+}$ at m/z 381.2.

Figure 5C:
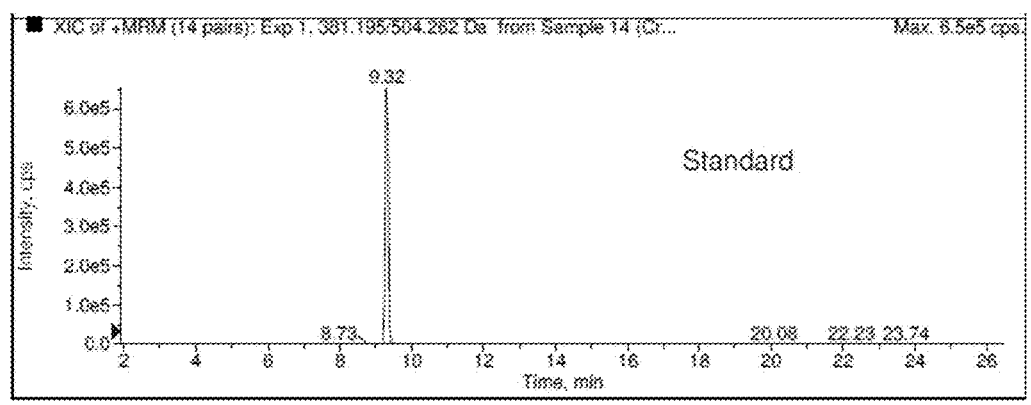

FIG. 5C sets forth an LC-MRM ion chromatogram of a standard polypeptide derived from the Cry34Ab1 polypeptide. The LC-MRM ion chromatogram of 381.2/504.3 is shown for the digested Cry34Ab1 standard.

Figure 6A:
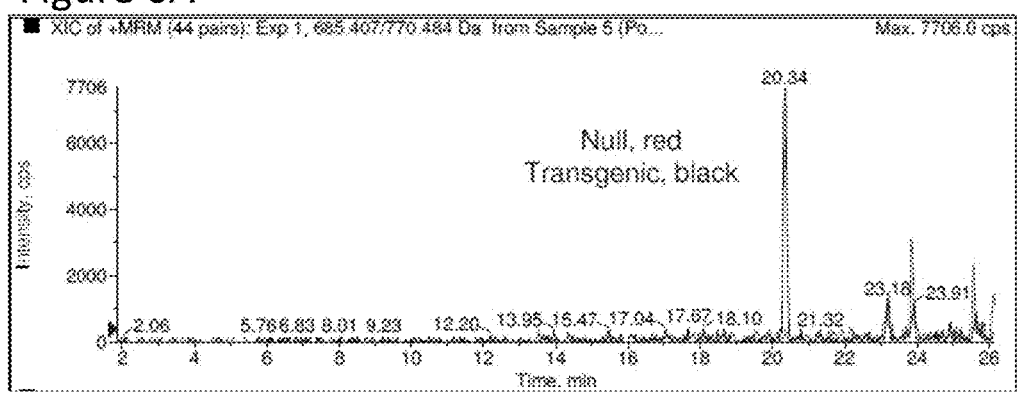

FIG. 6A sets forth overlays of LC-MRM ion chromatograms for transgenic plants (black), expressing a transgenic Cry35Ab1 polypeptide, and null plants (red) that do not express the Cry35Ab1 polypeptide. The product ion 770.5 m/z is shown for peptide VLTAGTGQALGLIR (SEQ ID NO: 7), $[M+2H]^{2+}$ at m/z 685.4.

Figure 6B:
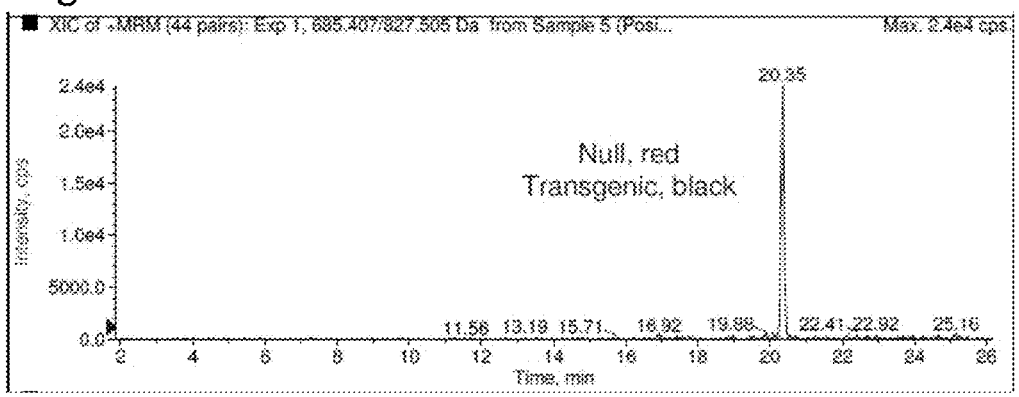

FIG. 6B sets forth overlays of LC-MRM ion chromatograms for transgenic plants (black), expressing a transgenic Cry35Ab1 polypeptide, and null plants (red) that do not express the Cry35Ab1 polypeptide. The product ion 827.5 m/z is shown for peptide VLTAGTGQALGLIR (SEQ ID NO: 7), $[M+2H]^{2+}$ at m/z 685.4.

Figure 6C:
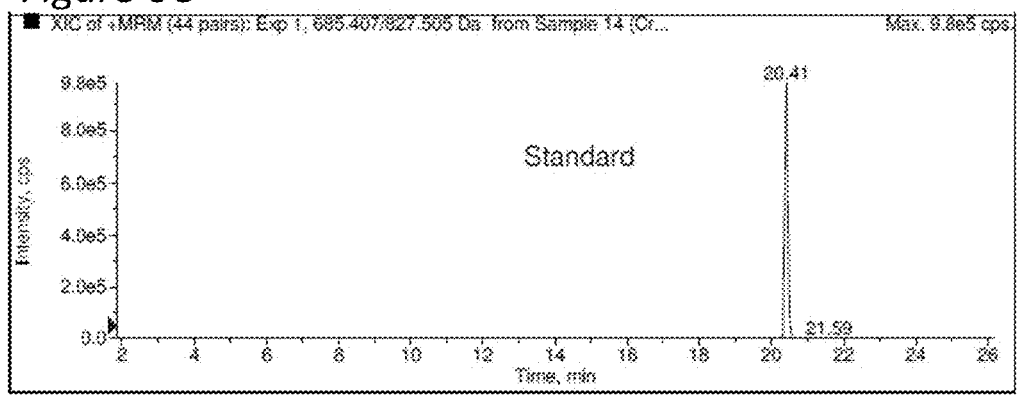

FIG. 6C sets forth an LC-MRM ion chromatogram of a standard polypeptide derived from the Cry35Ab1 polypeptide. The LC-MRM ion chromatogram of 685.4/827.5 is shown for the digested Cry35Ab1 standard.

DETAILED DESCRIPTION OF THE INVENTION

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

A method is provided for detecting at least one polypeptide of interest in a plant or a plurality of plants without the use of a reference standard. The method comprises the steps of obtaining a first sample from one or more plants expressing the polypeptide of interest and obtaining a second sample from at least one negative control plant that does not express the polypeptide of interest. Analysis is performed according to an information-dependent acquisition (IDA) method using liquid chromatography-tandem mass spectrometry (LC-MS/MS) and databases to detect and identify tryptic peptides derived from the polypeptide of interest in the sample. The method then determines whether the polypeptide of interest is present in the plant or plants by using retention times obtained by the IDA method and comparing chromatograms of the first sample and the second sample. The sensitivity and specificity of the method allows for detection of the polypeptide of interest directly from crude extract without the need for sample cleanup or enrichment. Alternatively, the method can be used to detect the absence or suppression of at least one polypeptide of interest in a plant or a plurality of plants without the use of a reference standard. The method comprises the steps of obtaining a first sample from one or more plants wherein expression of the polypeptide of interest is suppressed, for example, a plant comprising a knock out mutation, a suppression transgene, or comprising or exposed to a RNAi composition, and obtaining a second sample from at least one control plant that does express the polypeptide of interest.

The method can further be used to determine the relative expression level of the polypeptide of interest. In this manner, the chromatogram peaks associated with the polypeptide of interest are integrated and the relative expression level of the polypeptide of interest is determined in each plant, wherein a higher relative expression level is indicated by a larger integrated peak value. The method can further comprise the step of selecting one or more plants having a higher relative expression level of the polypeptide of interest. Such plants can be used in breeding programs.

In further embodiments, the methods disclosed herein also comprise the use of synthetic peptides or recombinant polypeptides to confirm the presence of the polypeptide of interest in the plant or plurality of plants.

As used herein, a "negative control plant" specifically refers to a plant that does not express the polypeptide of interest and is used as a comparative reference point for plants that do express the polypeptide of interest. A negative control plant can comprise, for example: (a) a wild-type plant, i.e., of the same genotype as the starting material for the genetic alteration which resulted in a plant expressing the polypeptide of interest; (b) a plant of the same genotype as the starting material but which has been transformed with a null construct (i.e., with a construct which has no known effect on a trait of interest, such as a construct comprising a marker gene); (c) a plant that is a non-transformed segregant among progeny of the plant expressing the polypeptide of interest; or (d) a plant genetically identical to the plant expressing the polypeptide of interest but which is not exposed to conditions or stimuli that would induce expression of the polypeptide of interest. In specific embodiments, a negative control plant is a non-transgenic plant or, alternatively, a transgenic plant that does not express the polypeptide of interest. In regards to detecting suppression of a polynucleotide of interest, a "control plant" expressing the polypeptide of interest is used as a comparative reference point for plants wherein expression of the polypeptide of interest is suppressed. As for a negative control plant, the control plant can be (a) a wild-type plant, i.e., of the same genotype as the starting material for the genetic alteration which resulted in a plant suppressing the polypeptide of interest; (b) a plant of the same genotype as the starting material but which has been transformed with a null construct (i.e., with a construct which has no known effect on a trait of interest, such as a construct comprising a marker gene); (c) a plant that is a non-transformed sergeant among progeny of the plant suppressing the polypeptide of interest; or (d) a plant genetically identical to the plant suppressing the polypeptide of interest but which is not exposed to conditions or stimuli that would induce suppression of the polypeptide of interest.

II. Liquid Chromatography-Tandem Mass Spectrometry

The methods disclosed herein comprise an information-dependent acquisition (IDA) method that utilizes liquid chromatography-tandem mass spectrometry (LC-MS/MS) and databases to detect the presence of a polypeptide of interest in a plant or determine the relative expression level of a polypeptide of interest in a plurality of plants.

As used herein, liquid chromatography (LC) is a technique used to separate analytes of interest from one another in a mixture of compounds, or from other constituents in a test sample, for the purpose of identifying, quantifying or purifying the individual components of the mixture. Liquid chromatography typically comprises the use of a high performance liquid chromatography (HPLC) column. Any HPLC column that can sufficiently resolve the analyte of interest (i.e., tryptic peptides derived from a polypeptide of interest) and allow for its detection according to the method can be employed. Suitable liquid chromatography systems and HPLC columns would be known to those of ordinary skill in the art.

In LC-MS/MS, liquid chromatography is used in conjunction with tandem mass spectrometry (MS/MS) to detect, identify, and/or quantify one or more polypeptides of interest in a sample prepared from a plant. As used herein, "mass spectrometry" or "MS" generally refers to methods of filtering, detecting, and measuring ions based on their mass-to-charge ratio, or "m/z." In mass spectrometry, one or more molecules of interest are ionized, and the ions are subsequently introduced into a mass spectrographic instrument (i.e., a mass spectrometer) where, due to a combination of magnetic and electric fields, the ions follow a path in space that is dependent upon their mass ("m") and charge ("z"). See, e.g., U.S. Pat. No. 6,107,623, entitled "Methods and Apparatus for Tandem Mass Spectrometry," which is hereby incorporated by reference in its entirety. As used herein, "tandem mass spectrometry" or "MS/MS" refers to any method comprising multiple steps of mass spectrometry selection with fragmentation occurring between the selection stages.

Mass spectrometers that can be utilized in the methods disclosed herein typically comprise three components: an ionization source, one or more mass analyzers, and a detector. Methods of ionization that are suitable for use include, but are not limited to, chemical ionization, electron ionization, inductively coupled plasma, glow discharge, field desorption, fast atom bombardment, atmospheric pressure chemical ionization, spark ionization and thermal ionization. Types of mass analyzers that can be useful include, but are not limited to, mass analyzer systems that include two mass separators with an ion fragmentor disposed in the ion flight path between the two mass separators. Examples of suitable mass separators include, but are not limited to, quadrupoles, RF multipoles, ion traps, time-of-flight (TOF), and TOF in conjunction with a timed ion selector. Suitable ion fragmentors include, but are not limited to, those operating on the principles of: collision-induced dissociation (CID, also referred to as collisionally-assisted dissociation (CAD)), photo-induced dissociation (PID), surface-induced dissociation (SID), post source decay, or combinations thereof.

Suitable ion sources for the mass spectrometry systems include, but are not limited to, electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. One of several desirable features of ESI is that fractions from the chromatography column can proceed directly from the column to the ESI ion source.

Examples of suitable mass spectrometry systems for the mass analyzer include, but are not limited to, those which comprise a triple quadrupole, a quadrupole-linear ion trap, a quadrupole TOF systems, and TOF-TOF systems. In a specific embodiment, the methods disclosed herein utilize a hybrid triple quadrupole mass analyzer. In further embodiments, the hybrid triple quadrupole mass analyzer can be run in multiple reaction monitoring (MRM) mode or linear ion trap mode.

III. Method of Detecting a Polypeptide of Interest in a Plant

In one aspect, the invention provides a method of detecting a polypeptide of interest in a plant without the use of a reference standard. As used herein, a "reference standard" refers to any composition including, but not limited to, recombinant polypeptides or synthetic peptides, that can be used to identify and/or detect the presence of a polypeptide of interest in a sample prepared from a plant.

The method comprises a first step of obtaining a plant expressing the polypeptide of interest and a negative control plant that does not express the polypeptide of interest. Plants obtained for use in the method are described elsewhere herein. Samples are prepared from both the plant and the negative control plant for analysis. As used herein, the term "prepared," and derivations thereof, is intended to mean any methods which allow for the isolation or purification of an analyte of interest (i.e., the polypeptide of interest) from a sample matrix or a sample derived therefrom, or any procedure that enriches the amount of one or more analytes of interest relative to one or more other components present in the sample matrix. The step of preparing a sample can be used to increase the sensitivity of the method including, but not limited to, reducing the dynamic range of the polypeptide concentration in the sample, increasing the relative concentration of the polypeptide of interest in the sample, and combinations thereof.

The step of preparing a sample can be used to remove one or more components of a sample that could interfere with the detection of the analyte. For example, such components could be those that interfere with detection of an analyte ion by mass spectrometry. In other embodiments, the step of preparing a sample is used to remove the analyte of interest from the test sample matrix. Various preparation techniques can be employed to extract or purify an analyte of interest from a sample, and the selection of extraction techniques appropriate for extracting an analyte of interest from specific plants, or cells, or plant parts, would be known to those of ordinary skill in the art. In a particular embodiment, samples are prepared from the plants of the method(s) using the techniques described in the Examples provided herein.

When preparing a sample from a positive plant or a negative control plant, such samples can be treated to generate proteolytic fragments of the polypeptide of interest for analysis. Suitable techniques for generating proteolytic fragments include any sequence-specific cleavage process, examples of which include cleavage with proteases such as serine proteases or thiol proteases. In one embodiment, a plurality of proteolytic fragments (e.g., peptides) can be generated from a polypeptide by the enzymatic hydrolysis of peptide bonds with trypsin.

Samples prepared from the positive plant or negative control plant of the method are subjected to an information-dependent acquisition (IDA) method. The IDA method utilizes liquid chromatography-tandem mass spectrometry (LC-MS/MS) and databases to detect the presence of the polypeptide of interest in a plant. The IDA method comprises a first step of predicting all tryptic peptides that can be derived from the polypeptide of interest following proteolytic fragmentation or digestion, based on the known or predicted amino acid sequence of the polypeptide. The amino acid sequence of the polypeptide of interest can be determined by any method known to those of ordinary skill in the art, including the use of amino acid sequence databases (e.g., Celera, SwissProt, etc.), DNA databases, translations of a gene sequence, direct experimental determination, or combinations thereof. In certain embodiments, the predicted tryptic peptides have a length of about 1 to 30 amino acids or about 6 to 20 amino acids. In additional embodiments, the predicted tryptic peptides are within the Q1 range of about 300 to 1200 m/z or about 350 to 900 m/z. Multiple reaction monitoring (MRM) transitions and collision energies are also predicted for each of the predicted tryptic peptides. The predicted MRM transitions can include one or more of the daughter ions predicted for the corresponding tryptic peptide. The tryptic peptides, MRM transitions, and collision energies can be predicted using any suitable method or software known in the art including, but not limited to, MIDAS Workflow Designer (AB Sciex).

The IDA method further comprises the step of performing a survey scan of the samples prepared from the plant and the negative control plant. The survey scan of the method utilizes LC-MS/MS to monitor the sample for the predicted MRM transitions of the predicted tryptic peptides. In the survey scan, tandem mass spectrometry is performed on each sample in MRM mode, and LC-MRM ion chromatograms are produced for each sample. LC-MRM ion chromatograms are known to those of ordinary skill in the art and plot the intensity of signals observed (y-axis) over time (x-axis) for an MRM transition.

As used herein, "multiple reaction monitoring," "MRM," or "MRM mode" means a mass spectrometry method wherein a triple quadrupole type of instrument is used to select and analyze a specific analyte, such as a tryptic peptide derived from the polypeptide of interest. The first quadrupole of a triple quadrupole mass spectrometer, herein referred to as Q1, acts as a first mass separator. The transmitted mass-to-charge (m/z) range of Q1 is selected to transmit a molecular ion, often referred to as the "parent ion" or the "precursor ion," to the second quadrupole, herein referred to as Q2. This can be accomplished, for example, by setting Q1 to transmit ions in a mass window about 3 mass units wide substantially centered on the mass of a proteolytic fragment.

Q2 acts as an ion fragmentor (e.g., a collision cell, photodissociation region, etc.) that can be maintained at a sufficiently high pressure and voltage so that multiple low energy collisions occur, producing fragment ions, often referred to as "daughter ions." Q2 can comprise a collision gas for conducting collision-induced dissociation (CID) and a quadrupole to facilitate the collection and transmittal of daughter ion fragments to a third quadrupole, referred to herein as Q3.

Q3 acts as a second mass separator. The transmitted m/z range of Q3 is selected to transmit one or more daughter ions to a detector which measures the daughter ion signal. This can be accomplished by setting Q3 to transmit ions in a mass window about 1 mass unit wide substantially centered on the mass of a daughter ion. Using MRM analysis, multiple polypeptides and multiple regions (signature peptides) of a polypeptide can be monitored in single run.

A monitored pair of parent ion and daughter ion masses can be referred to as an "MRM transition" or "parent-daughter ion transition." Where a parent ion is generated for a tryptic peptide, and the ion signal of the corresponding daughter ion is measured, the daughter ion signal at the detector is referred to as the "MRM transition signal." The MRM transition signal can be based on the intensity (i.e., the average, mean, maximum, etc.) of the daughter ion peak, the integrated area of the daughter ion peak, or any combination thereof.

Where the survey scan of the method is performed in MRM mode, the MRM parameters for each MRM transition to be monitored can be chosen to facilitate optimizing the signal for the selected daughter ion(s) associated with their corresponding parent ion. In particular embodiments of the method, 1, 2, 3, 4, 5, 10, 20, 30, 40, or up to a maximum of 50 MRM transitions are monitored and/or detected by the survey scan.

Where an individual MRM transition signal exceeds a predetermined threshold, the tandem mass spectrometer performs an information-dependent acquisition scan (IDA scan) of the tryptic peptide associated with the MRM transition signal. In a particular embodiment, the predetermined threshold is a number of counts per second that are significantly higher than the background noise of the survey scan. In other embodiments, the predetermined threshold for initiating the IDA scan can be about 10, 20, 30, 40, 50, 75, 100, 150, 200, 250, 300, 400, 500 or more counts per second. As used herein, the IDA scan of the method is an enhanced product ion (EPI) scan that is performed in linear ion trap mode to confirm the sequence of the tryptic peptide corresponding to the MRM transition signal. In one embodiment, an enhanced resolution (ER) scan can be performed after the survey scan and prior to the IDA scan to confirm the charge state and monoisotropic mass of the tryptic peptide associated with the MRM transition signal.

As used herein, an "enhanced product ion scan" or "EPI scan" means a mass spectrometry method used to obtain high quality MS/MS spectra on a specific ion. The fragmentation is done in the collision cell and provides MS/MS spectra typical of collisionally-activated dissociation (CAD) in the Q2 collision cell. The fragment ions generated are captured in an ion trap then scanned at speeds dependent upon the required fragment ion resolution.

As used herein, a "linear ion trap" or "linear ion trap mode" refers to the use of a set of quadrupole rods to confine ions radially and static electrical potential on-end electrodes to confine the ions axially. A linear ion trap can be used as a selective mass filter or as an actual trap by creating a potential well for ions along the axis of the electrodes. Where an individual MRM transition signal exceeds a predetermined threshold, the IDA scan is used in linear ion trap mode to produce a set of MS/MS spectra for the tryptic peptide associated with the MRM transition signal. An "MS/MS spectrum" or "MS/MS spectra" are known to those of ordinary skill in the art and refer to the mass spectra obtained from the IDA scan, which plot the mass to charge ratio (m/z) on the x-axis and the ion intensity on the y-axis.

The IDA scan of the method produces a set of MS/MS spectra for the tryptic peptide associated with the MRM transition signal. The set of MS/MS spectra are submitted to at least one protein database including the sequence of the protein of interest for peptide/protein identification using a search engine such as, but not limited to, MASCOT database (Matrix Science). In addition to tryptic peptide identification, the databases used in the method also provide the retention time of the identified tryptic peptide on its corresponding LC-MRM ion chromatogram.

The method further comprises the step of determining whether an MRM transition signal is present in the LC-MRM ion chromatograms from both the plant sample and the negative control plant sample at the retention time determined from the database(s). In the event that an MRM transition signal is present at the determined retention time in the plant sample, but absent at the determined retention time in the negative control plant sample, this indicates the presence of the polypeptide of interest in the plant. Determining whether an MRM transition signal is present in an LC-MRM ion chromatogram means observing whether a significant peak is present at the determined retention time, wherein significance can be determined by a person of ordinary skill in the art.

In a particular embodiment, the method can be used to detect a single polypeptide of interest in a plant. In other embodiments, the method can be used to detect 2, 3, 4, 5, 6, 7, 8, 9, 10 or more polypeptides of interest in a plant simultaneously, wherein the IDA method simultaneously monitors for, and analyzes, MRM transitions for tryptic peptides derived from multiple polypeptides of interest.

IV. Method of Determining the Relative Expression Level of a Polypeptide of Interest in a Plurality of Plants In another aspect, the invention encompasses a method of determining the relative expression level of a polypeptide of interest in a plurality of plants without the use of a reference standard. As used herein, "relative expression level" means a qualitative comparison between the detected amount of the polypeptide of interest in two or more plants, determined by comparing the MRM transition signal(s) produced by tryptic peptides of the polypeptide of interest. The method comprises obtaining a plurality of plants expressing the polypeptide of interest and a negative control plant. A "plurality of plants" is intended to mean 2, 3, 4, 5, 10, 20, or more plants that comprise the polypeptide of interest. The plurality of plants can comprise equal amounts, or different amounts, of the polypeptide of interest.

According to the method, a first sample is prepared from a first plant, a second sample is prepared from a second plant, and a negative control sample is prepared from a negative control plant. Each sample is prepared for analysis in the method as described elsewhere herein. Each sample is also analyzed by the IDA method described elsewhere herein to determine whether an MRM transition signal is present at a determined retention time in the first plant sample and in the second plant sample, but absent at the determined retention time in the negative control plant sample. This event indicates the presence of the polypeptide of interest in the first plant and second plant. The presence of an MRM transition signal at a determined retention time in an LC-MRM ion chromatogram is also determined as described elsewhere herein.

The method further comprises the step of integrating the peaks associated with the MRM transition signals in the LC-MRM ion chromatograms of the first plant sample and the second plant sample. Integration of the peaks can be performed using any suitable methods known to those of ordinary skill in the art, yielding an integrated peak value. The method comprises the additional step of determining the relative expression level of the polypeptide of interest between the first plant and the second plant, wherein the relative expression level is determined by a comparison of the integrated peak values of the first plant and the second plant. A higher relative expression level in a plant is indicated by a larger integrated peak value for that plant when compared to another plant. Similarly, a lower relative expression level in a plant is indicated by a smaller integrated peak value for that plant when compared to another plant.

In a particular embodiment, the method further comprises the step of selecting the plant or plants having a higher relative expression level of the polypeptide of interest. In an additional embodiment, the method can be used to detect 2, 3, 4, 5, 10, or more polypeptides of interest simultaneously in the plurality of plants, wherein the IDA method simultaneously monitors for and analyzes MRM transitions for tryptic peptides derived from multiple polypeptides of interest.

V. Synthetic Peptides and Recombinant Polypeptides

In additional embodiments, the methods further utilize synthetic peptides and/or recombinant polypeptides to confirm the presence of a polypeptide of interest in a plant or in a plurality of plants. Synthetic peptides utilized in the method comprise the amino acid sequence of the tryptic peptide(s) associated with the MRM transition signal(s) that exceeded the predetermined threshold value in the survey scan of the IDA method. Such synthetic peptides can be produced by any suitable method known to those of ordinary skill in the art and are readily commercially available.

When using a synthetic peptide for confirmation in the method, a synthetic peptide sample is prepared for analysis. As previously described for plant samples, MRM transitions and collision energies are predicted for the synthetic peptide sample. The synthetic peptide sample is then subjected to the IDA method described elsewhere herein, with the exception that tryptic peptides are not predicted. LC-MRM ion chromatograms, MS/MS spectra, and retention time information are obtained for the synthetic peptide sample as previously described for plant samples. The method further comprises the step of comparing the LC-MRM ion chromatograms of the plant sample(s), the negative control plant sample, and the synthetic peptide sample at the determined retention time for the MRM transition signal associated with the tryptic peptide. The presence of the polypeptide of interest is confirmed in the plant(s) by the presence of an MRM transition signal at the determined retention time in the plant sample(s) and the synthetic peptide sample, and the absence of a corresponding MRM transition signal in the negative control plant sample. When the gene or protein of interest is endogenous to the plants, the presence of the polypeptide can also be confirmed similarly by the significant difference between the positive and negative samples.

Recombinant polypeptides utilized in the method comprise the amino acid sequence of the polypeptide of interest, or a fragment thereof. Such recombinant polypeptides can be produced by any suitable method known to those of ordinary skill in the art. When using a recombinant polypeptide for confirmation in the method, a recombinant polypeptide sample is prepared for analysis. As previously described for plant samples, tryptic peptides, MRM transitions, and collision energies are predicted for the recombinant polypeptide sample. The recombinant polypeptide sample is then subjected to the IDA method described elsewhere herein. LC-MRM ion chromatograms, MS/MS spectra, and retention time information are obtained for the recombinant polypeptide sample as previously described for plant samples. The method further comprises the step of comparing the LC-MRM ion chromatograms of the plant sample(s), the negative control plant sample, and the recombinant polypeptide sample at the determined retention time for the MRM transition signal associated with the tryptic peptide. The presence of the polypeptide of interest is confirmed in the plant(s) by the presence of an MRM transition signal at the determined retention time in the plant sample(s) and the recombinant polypeptide sample, and the absence of a corresponding MRM transition signal in the negative control plant sample.

The plants expressing the polypeptide of interest can be transgenic plants or non-transgenic plants. Where plants expressing the polypeptide of interest are non-transgenic, they can be produced by any method known in the art including, but not limited to, traditional breeding techniques, wherein one or more genes conferring a trait or phenotype of interest are bred into, and stably expressed in the plant.

Where the plants expressing the polypeptide of interest are transgenic, such plants can be produced by any recombinant DNA methods known in the art including, but not limited to, genetic alteration and transformation, wherein a gene of interest is affected or introduced into a plant. Alternatively, such plants can be descended from a transgenic plant or transgenic cell comprising a desired genetic alteration. The resulting transgenic plant can be grown under plant forming conditions known in the art for a time sufficient to modulate the concentration of the polypeptide of interest in the plant. Many methods are known in the art for providing a polypeptide to a plant including, but not limited to, transient or stable introduction of a polynucleotide construct encoding a polypeptide, or direct introduction of the polypeptide into the plant.

The sample from the plants to be used in the methods of the invention can be taken from any tissue if the polypeptide is constitutively expressed. Where the polypeptide of interest is expressed in a tissue-specific manner, the sample will comprise the tissue where the polypeptide of interest is expressed including leaves, roots, seeds, and the like. The tissue for the sample may be taken from a single plant or from a plurality of plants.

Any plant can be used in the methods of the invention including, but not limited to, monocots and dicots. Examples of plant species of interest include, but are not limited to, corn (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables of interest include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*.

Conifers of interest include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Hardwood trees can also be employed including ash, aspen, beech, basswood, birch, black cherry, black walnut, buckeye, American chestnut, cottonwood, dogwood, elm, hackberry, hickory, holly, locust, *magnolia*, maple, oak, poplar, red alder, redbud, royal *paulownia, sassafras*, sweetgum, sycamore, tupelo, willow, yellow-poplar.

In specific embodiments, plants used in the methods disclosed herein are crop plants (i.e., corn, alfalfa, sunflower, *Brassica*, soybean, cotton, safflower, peanut, *sorghum*, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Other plants of interest include turfgrasses such as, for example, turfgrasses from the genus *Poa, Agrostis, Festuca, Lolium*, and *Zoysia*. Additional turfgrasses can come from the subfamily Panicoideae. Turfgrasses can further include, but are not limited to, Blue gramma (*Bouteloua gracilis* (H.B.K.) Lag. Ex Griffiths); Buffalograss (*Buchloe dactyloids* (Nutt.) Engelm.); Slender creeping red fescue (*Festuca rubra* ssp. *Litoralis*); Red fescue (*Festuca rubra*); Colonial bentgrass (*Agrostis tenuis* Sibth.); Creeping bentgrass (*Agrostis palustris* Huds.); Fairway wheatgrass (*Agropyron cristatum* (L.) Gaertn.); Hard fescue (*Festuca longifolia* Thuill.); Kentucky bluegrass (*Poa pratensis* L.); Perennial ryegrass (*Lolium perenne* L.); Rough bluegrass (*Poa trivialis* L.); Sideoats grama (*Bouteloua curtipendula* Michx. Ton.); Smooth bromegrass (*Bromus inermis* Leyss.); Tall fescue (*Festuca arundinacea* Schreb.); Annual bluegrass (*Poa annua* L.); Annual ryegrass (*Lolium multiflorum* Lam.); Redtop (*Agrostis alba* L.); Japanese lawn grass (*Zoysia japonica*); bermudagrass (*Cynodon dactylon; Cynodon* spp. L.C. Rich; *Cynodon transvaalensis*); Seashore paspalum (*Paspalum vaginatum* Swartz); Zoysiagrass (*Zoysia* spp. Willd; *Zoysia japonica* and *Z. matrella* var. *matrella*); Bahiagrass (*Paspalum notatum* Flugge); Carpetgrass (*Axonopus affinis* Chase); Centipedegrass (*Eremochloa ophiuroides* Munro Hack.); Kikuyugrass (*Pennisetum clandesinum* Hochst Ex Chiov); Browntop bent (*Agrostis tenuis* also known as *A. capillaris*); Velvet bent (*Agrostis canina*); Perennial ryegrass (*Lolium perenne*); and, St. Augustinegrass (*Stenotaphrum secundatum* Walt. Kuntze). Additional grasses of interest include switchgrass (*Panicum virgatum*).

Any polypeptide of interest can be examined using the methods disclosed herein. Such polypeptides can be reflective of the commercial markets and interests of those involved in the development of crops. General categories of polypeptides of interest include, for example, those polypeptides involved in information, such as zinc fingers, those involved in communication, such as kinases, and those involved in housekeeping, such as heat shock proteins. More specific categories of polypeptides, for example, include polypeptides that contribute to important traits for agronomics, insect resistance, disease resistance, herbicide resistance, sterility, grain characteristics, and commercial products. Polypeptides of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Polypeptides of interest can be made by site-directed mutagenesis of coding sequences to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other polypeptides include methionine-rich plant polypeptides such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261: 6279; Kirihara et al. (1988) *Gene* 71:359; both of which are herein incorporated by reference); and rice (Musumura et al. (1989) *Plant Mol. Biol.* 12:123, herein incorporated by reference). Other agronomically important polypeptides include latex, Floury 2, growth factors, seed storage factors, and transcription factors.

Polypeptides that affect insect resistance can induce resistance to pests that have great yield drag such as rootworm, cutworm, European Corn Borer, and the like. Such polypeptides include, for example, *Bacillus thuringiensis* toxic protein polypeptides (U.S. Pat. Nos. 5,366,892; 5,747,450; 5,736,514; 5,723,756; 5,593,881; and Geiser et al. (1986) *Gene* 48:109); and the like.

Polypeptides affecting disease resistance traits include detoxification polypeptides, such as against fumonosin (U.S. Pat. No. 5,792,931); avirulence (avr) and disease resistance (R) polypeptides (Jones et al. (1994) *Science* 266:789; Martin et al. (1993) *Science* 262:1432; and Mindrinos et al. (1994) *Cell* 78:1089); and the like.

Herbicide resistance traits can include polypeptides affecting resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), polypeptides affecting resistance to herbicides that act to inhibit action of glutamine synthase, such as phosphinothricin or basta (e.g., the bar gene); glyphosate (e.g., the EPSPS gene and the GAT gene; see, for example, U.S.

Publication No. 20040082770 and WO 03/092360); or other such polypeptides known in the art. The bar gene encodes a polypeptide that confers resistance to the herbicide basta, the nptII gene encodes a polypeptide that confers resistance to the antibiotics kanamycin and geneticin, and the ALS-gene mutants encode a polypeptide that confers resistance to the herbicide chlorsulfuron. Sterility polypeptides can also be encoded by genes in an expression cassette and provide an alternative to physical detasseling. Examples of polypeptides used in such ways include male tissue-preferred polypeptides and polypeptides with male sterility phenotypes such as QM, described in U.S. Pat. No. 5,583, 210. Other polypeptides include kinases and those polypeptides that are toxic to either male or female gametophytic development.

The quality of grain is reflected in traits such as levels and types of oils, saturated and unsaturated, quality and quantity of essential amino acids, and levels of cellulose. In corn, modified hordothionin polypeptides are described in U.S. Pat. Nos. 5,703,049, 5,885,801, 5,885,802, and 5,990,389.

Commercial traits can also be affected by polypeptides that could increase for example, starch for ethanol production, or provide expression of proteins. Another important commercial use of transformed plants is the production of polymers and bioplastics such as those described in U.S. Pat. No. 5,602,321. Polypeptides such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including prokaryotes and other eukaryotes. Such products include enzymes, cofactors, hormones, and the like. The level of polypeptides, particularly modified polypeptides having improved amino acid distribution to improve the nutrient value of the plant, can be increased. This is achieved by the expression of such polypeptides having enhanced amino acid content.

The article "a" and "an" are used herein to refer to one or more than one (i.e., to at least one) of the grammatical object of the article. By way of example, "an element" means one or more element.

Although the foregoing invention has been described in some detail by way of illustration and example for purposes of clarity of understanding, it will be obvious that certain changes and modifications can be practiced within the scope of the appended claims.

EXAMPLES

The Examples disclosed herein describe one embodiment of the invention, wherein five proteins in transgenic maize leaf extracts are identified: two proteins that provide herbicide resistance, namely, gene-shuffled glyphosate acetyltransferase variant (GAT4621) and phosphinothricin acetyltransferase (PAT) (Castle et al., *Science* 2004, 304, 1151-1154; Block et al., *EMBO J.* 1987, 6, 2513-2518); and three insecticidal proteins, namely, Cry1F, Cry34Ab1 and Cry35Ab1 (U.S. EPA Pesticide Fact Sheet—*Bacillus thuringiensis* Cry1F protein; U.S. EPA Pesticide Fact Sheet—*Bacillus thuringiensis* Cry34Ab1 and Cry35Ab1 proteins). The method disclosed herein was used to selectively detect putative peptides for each protein of interest.

Example 1

Materials and Sample Preparation

All chemicals used in the present Examples were purchased from VWR International (Radnor, Pa.), unless otherwise noted. The extraction buffer used was 8 M urea with 5 mM dithiothreitol (DTT) and 0.05% Tween 20. This extraction buffer was chosen because it was found to help the tryptic digestion of Bt crystalline (Cry) proteins, namely Cry1F, Cry34Ab1, and Cry35Ab1. When analyzing only non-Cry proteins, such as GAT4621 and PAT, a more convenient extraction buffer such as phosphate-buffered saline and 0.05% Tween 20 (PBST) could be used. The digestion buffer contained 100 mM ammonium bicarbonate (ABC) without pH adjustment. Recombinant protein standards were digested in 100 mM ABC with 0.05% Tween 20 (ABCT). As described herein, protein standards are not necessary for the detection of proteins in plants using the disclosed method; however, protein standards were available and were chosen in place of synthetic peptides. The reducing agent was 0.25 M DTT and the alkylating agent was 0.3 M iodoacetamide (IAA). Mass spectrometry grade trypsin was purchased from G-Biosciences (Geno Technology, Inc., St. Louis, Mo.).

Transgenic and null (non-transgenic) maize plants were grown in the greenhouse facilities of DuPont Pioneer at Johnston, Iowa. The maize leaves were harvested at approximately stage V5-V6 and ground after lyophilization. Recombinant protein standards were expressed in *Escherichia coli* and purified internally by the Protein Core Facility (DuPont Pioneer). Aliquots were stored at −80° C. for single usage. Protein purities (>95%) were determined by sodium dodecyl sulfate-polyacrylamide gel electrophoresis (SDS-PAGE). Protein concentrations were determined by amino acid analysis (Keck Facility, Yale University).

A total of 300 μL of extraction buffer was added per 10 mg leaf tissue, weighed into 1.2 mL microtiter tubes (Quality Scientific Plastics, San Diego, Calif.). Both transgenic and null samples were run in triplicate. Samples were mixed in a SPEX Certiprep 2000 GenoGrinder (SPEX SamplePrep, Metuchen, N.J.) at a setting of 1600 strokes/min for 60 s and then centrifuged (4° C., 3000 rpm) for 15 min. A total of 20 μL of supernatant was added to 0.2 mL thin wall polymerase chain reaction (PCR) strip tubes (Axygen Scientific, Inc., Union City, Calif.). An appropriate volume of each recombinant protein standard was added to 100 M ABCT buffer for a total volume of 100 μL. The volume of standard added was determined such that a final on-column load of 5000 fmol was achieved. All samples were heated at 95° C. for 15 min in an oven (VWR International) in order to deactivate non-specific proteases. Following heating, a total of 100 μL of digestion buffer (100 mM ABC buffer) was added to each sample. To both samples and standards, 6 μL of 0.25 M DTT were added. The PCR tubes were then incubated at 50° C. for 30 min. After reduction, 6 μL of 0.3 M IAA were added and the PCR tubes were incubated at room temperature in the dark for 30 min. Next, 10 μl of 0.4 μg/μL trypsin were added. Trypsin digestion (45° C., 30 min) was performed in a homemade sample holder fitted into a CEM Discover Proteomics System (CEM Corporation, Matthews, NC). The PCR tubes were mixed and briefly spun in a microcentrifuge after each reagent addition described in the steps above. Following digestion, acidification was done by addition of 10 μL of 10% (v/v) formic acid.

Example 2

Information Dependent Acquisition Analysis Using LC-MS/MS

The LC-MS/MS system used in the present Examples included an AB Sciex 5500 Q-TRAP (AB Sciex, Framingham, Mass.) with a Turbo ion-spray source and Waters Acquity ultra-performance liquid chromatography (UPLC) (Waters Corporation, Milford, Mass.).

Instrument control and data acquisition were handled by Analyst 1.5.2 software (AB Sciex). The autosampler temperature was maintained at 4° C. A total of 20 μL was injected onto an Aquasil, 100×2.1 mm, 3 μm, C18 column (Thermo Fisher Scientific, Waltham, Mass.), which was maintained at 60° C. The LC flow rate was 0.25 mL/min, unless otherwise noted. Mobile phases consisted of 0.1% formic acid (MPA) and 0.1% formic acid in acetonitrile (MPB). The LC run started at 2% MPB for 2 min, followed by a 30 min linear gradient to 35% MPB. To wash the column, the UPLC flow was increased to 0.8 mL/min at 90% MPB for 5 min. During the wash, the flow was diverted to waste. After the wash, the flow returned to initial conditions for 3 minutes for column equilibration. The total run time for each injection was ~45 min.

MIDAS Workflow Designer 1.1.0 (AB Sciex) was used to generate an IDA method which included a list of MRM transitions, along with collision energies, for all tryptic peptides of length 6-20 amino acids (no missed cleavages allowed) within the Q1 range of 350 to 900 m/z. One fixed modification was selected for carbamidomethyl cysteine. For each peptide, one or two product ions (the first one or two product ions with m/z larger than the precursor m/z) were chosen depending on the number of available peptides and a maximum of 50 MRM transitions were allowed per method. The MRM transitions were run at unit resolution in both Q1 and Q3. The dwell time was dependent on the number of MRM transitions with total scan time ~1 sec. Source parameters were as follows: curtain gas (CUR), 25; collision gas (CAD), medium; ion spray voltage, 5500 V; ion source temperature, 450° C.; both ion source gas 1 (GS1) and gas 2 (GS2), 50.

The IDA scans (EPI) were triggered if the MRM transition met the specified threshold of 300 counts per second (cps). Up to three of the most intense peaks were selected for fragmentation with no exclusion of former target ions. An Enhanced Resolution (ER) scan was not included in the IDA experiment to confirm the charge state because of low concentration of our target proteins of interest and the presence of potential interference in the complex crude sample extract. The use of the ER scan could prevent the target ions from being selected for MS/MS fragmentation because, although the low concentration target ion may be detectable by MRM, it could be below the noise level of the MS (ER) mode. The sensitivity and selectivity of the MRM mode allows for detection of low concentration ions more so than a MS scan such as ER. The EPI parameters were as follows: scan rate 10,000 Da/s, Q1 resolution unit, fixed LIT fill time 30 ms, and a range of 100 to 1,000 Da.

For convenience one IDA method was created for each protein; therefore, each sample was injected five times in order to detect all five proteins. Technically, one IDA method can be used to analyze multiple proteins with one injection as long as there are not too many MRM transitions in one method.

Example 3

Database Search and Target Protein Identification

The resulting LC-MS/MS data were submitted for target protein identification to a local Mascot server 2.3.1 (Matrix Science, London, UK) using Mascot Daemon 2.3.2 (Matrix Science) or the Mascot script embedded in the Analyst software. The following MS/MS ion search parameters were used: centroid MS/MS data, charge state not determined from the MS scan because ER was not included in the experiments, fixed modification of carbamidomethylation (C), and variable modifications of oxidation (M) and deamidation (NQ). The mass tolerance was set to ±0.5 Da for MS and 0.6 Da for MS/MS; up to one missed cleavage was allowed. When the Mascot peptide summary report was generated, significance threshold (p<0.05) and standard scoring were used.

The LC-MS/MS data were searched against two combined protein databases. The first database contained all plant (Viridiplantae) sequences downloaded from UniProt. The second database was a small in-house database that contained all target transgenic protein sequences. Separation of the two databases simplified maintenance of the small database of custom sequences.

Example 4

Identification of Target Proteins with MRM-Initiated Detection and Sequencing (MIDAS) and Database Search After one IDA method for each protein was run on both transgenic and null unenriched crude extract samples, the MS/MS spectra from the IDA data were submitted to a protein database using Mascot MS/MS ion search for protein identifications. All five target proteins, namely GAT4621, PAT, Cry1F, Cry34Ab1 and Cry35Ab1, were identified in the transgenic samples. In contrast, none of the five proteins were identified in the null samples. At least two tryptic peptides were detected for each of the five target proteins.

The MS/MS spectra of three peptides that enabled detection of the GAT4621 protein are shown as an example in FIG. 1. The sequences of the peptides along with the observed y fragment ions are indicated in the figure. The peptide ion scores for these three peptides were 43 (FIG. 1A), 39 (FIG. 1B), and 33 (FIG. 1C), respectively. The Mascot ion score is based on the probability that a match between the experimental data and the theoretical sequence database entry is a random event (Perkins et al., *Electrophoresis* 1999, 20, 3551-3567). The Mascot peptide summary report provides guidance whether a score represents homology or identity. For these three peptides, a score greater than ~38 indicated homology while a score greater than ~46 indicated identity.

In generating the Mascot peptide summary report, the ion score cut-off was kept to zero with the recognition that false or random matches can happen due to noise in peptide fragmentation or co-eluting peptides. The methodology of the invention can tolerate high false positive hits from the Mascot MS/MS ion search results, which are not the final evidence for peptide identification. In fact, we rely more on the direct comparison of MRM signals of positive (transgenic) and negative (null, non-transgenic) samples were more heavily replied upon, and the ultimate evidence for the peptide identification comes from LC-MRM results of synthetic peptides or recombinant proteins, if available (see the Examples herein below). In essence, the Mascot search results were used to find potentially identified peptides so that MRM signals do not need to be inspected for every peptide, which might be tedious for large proteins with many tryptic peptides. Equally important is the retention time information which is also available from the Mascot search results. In contrast, if the ion score cut-off is set high, positive samples may receive negative hits because not all product ions are generated or detected in every experiment and only one or two product ions may be generated with a high enough signal to be detected for very low abundance peptides. For the same reason, the MRM threshold for triggering the IDA scan (EPI) was set low (300 cps) because the methodology is tolerant of high false positive hits in the Mascot search results.

The peptide score and retention time from the Mascot search results for one selected peptide from each of the five target proteins in the samples (two transgenic samples, TG1 and TG2, with triplicates of each sample) are shown in Table 1 below.

TABLE 1

Peptide Mascot search results for a selected peptide for each of the five target proteins with their retention times (RT).

| | Protein | | | | | | | | | |
|---|---|---|---|---|---|---|---|---|---|---|
| | GAT4621 | | PAT | | Cry1F | | Cry34Ab1 | | Cry35Ab1 | |
| | Peptide (SEQ ID) | | | | | | | | | |
| | HAEEILR (SEQ ID NO: 3) | | LHEALGYTAR (SEQ ID NO: 4) | | SATPTNTIDPER (SEQ ID NO: 5) | | TGHTLQLEDK (SEQ ID NO: 6) | | VLTAGTGQALGLIR (SEQ ID NO: 7) | |
| Sample | Score | RT (min) | Score | RT (min) | Score | RT (min) | Score | RT (min) | Score | RT (min) |
| TG1_1 | 27 | 8.2 | 26 | 10.6 | 35 | 10.8 | 28 | 9.3 | 53 | 20.3 |
| TG1_2 | 33 | 8.2 | 17 | 10.6 | 44 | 10.8 | 31 | 9.3 | 38 | 20.4 |
| TG1_3 | 33 | 8.2 | 30 | 10.6 | 49 | 10.8 | 33 | 9.3 | 60 | 20.4 |
| TG2_1 | 40 | 8.3 | 32 | 10.8 | 34 | 10.8 | 19 | 9.4 | 36 | 20.5 |
| TG2_2 | 37 | 8.3 | 27 | 10.8 | 26 | 10.8 | 32 | 9.4 | 32 | 20.5 |
| TG2_3 | 35 | 8.3 | 32 | 10.8 | 21 | 10.8 | 31 | 9.4 | 25 | 20.5 |
| Standard | 52 | 8.2 | 57 | 10.7 | 49 | 10.8 | 31 | 9.3 | 88 | 20.4 |

Repeatability of the peptides identified in the sample replicates is good, although it is understood that variation in the peptides identified is likely to occur given variations in MS/MS fragmentation, small changes in chromatography, or in differences in the peptides selected for fragmentation (Tabb et al., *J. Proteome Res.* 2010, 9, 761-776). It is worth noting that the five low concentration target proteins (as low as ~30 ppm for GAT4621 protein, based on dry weight, data not shown) were detected without much interference from major proteins such as Ribulose-1,5-bisphosphate carboxylase oxygenase (RuBisCO) in the leaf extract, fully demonstrating superior selectivity and sensitivity of the MIDAS approach of the invention. It is expected to be almost impossible to identify such low concentration proteins if using a non-target proteomics approach in which a MS scan is used as the survey scan. In a non-target proteomics approach, the most abundant proteins such as RuBisCO will be identified, while low abundance proteins may not be detected as their signals may be masked by high abundance proteins. In order to detect low abundance proteins with a non-target proteomics approach, additional cleanup or enrichment by use of a RuBisCO removal column or in-gel digestion may be needed.

Example 5

Identification of Target Proteins with LC-MRM

For peptide identification, the LC-MRM approach is generally more sensitive than MS/MS peptide search. As shown in FIG. 1, not all product ions have the same intensity. For peptides to be identified by MS/MS peptide search, multiple if not all product ions must be detected (see FIG. 1A, a peptide with a high peptide score). On the other hand, the LC-MRM approach only needs one or two most intense signature product ions (see FIG. 1C, a peptide with a low peptide score). However, the LC-MRM approach does need peptide standards to get retention times, which are chromatography dependent and are still challenging to standardize across different laboratories.

In the IDA experiments used herein, the LC-MRM signals for each potential peptide are acquired in the data files and those MRM chromatograms are available to be explored. With transgenic crops, the present methods have the unique advantage that true negative samples (null) are readily available for direct comparison with the transgenic samples in question. As discussed in the previous section, the Mascot search results help identify the peptides that were potentially detected and provide the retention time of those peptides. With both pieces of information, the MRM signals for the potentially detected peptides can be compared in transgenic and null samples.

FIGS. 2 through 6 show overlays of transgenic and null sample-extracted ion chromatograms (XIC) for one selected peptide from each of the five target proteins, with two MRM transitions shown for each peptide. Direct comparison of the null and the transgenic sample chromatograms clearly show unique MRM peaks present in the transgenic samples with the correct retention times (as determined by the Mascot search results) and these peaks absent in the null samples. In addition, the two MRM peaks (different product ions) for each peptide always have the same retention time.

It is also worth noting that, for most XICs shown in FIGS. 2-6, quite a few other peaks at the wrong retention times were detected, indicating that MRM without retention time information does not have enough selectivity for such complex samples. Since it is assumed that the null samples are ideal negative controls for the transgenic samples, and that the only difference between them is the target gene and/or proteins, it is tempting to conclude that these five target proteins are detected in the transgenic samples based upon the Mascot search results of transgenic samples (despite sometimes low peptide ion scores) and direct comparison of the LC-MRM signals for some peptides between transgenic and null samples. However, in this study, ultimate confirmation of target protein detection is further obtained by comparing the LC-MRM of synthetic peptides or recombinant proteins to the LC-MRM of the transgenic samples.

Example 6

Evidence of Peptide Identification by Synthetic Peptides or Recombinant Proteins The IDA approach used in the present invention combines the superior selectivity and sensitivity of MRM scans with the peptide sequencing capabilities of MS/MS. As described in this Example, physical confirmation of peptide identification is further obtained. It is understood that when MS/MS spectra are searched against a protein database, the experimental data (MS/MS) are compared to calculated peptide fragment ions, and thus peptides not proteins are matched. The proteins are inferred from the peptides. It is also understood that the peptide matching by MS/MS ion search is never achieved with 100% confidence, even for high score peptides, since MS/MS ion search is based on probability matching between the experimental MS/MS data and the calculated peptide fragment ions from a database sequence. Depending on the quality of both the experimental data and the database, a significant or best match might not be the correct match.

Therefore, the ultimate evidence for peptide and protein identifications relies on the synthetic peptides, and that recombinant proteins, when available, can substitute for multiple synthetic peptides. Synthetic peptides add an additional dimension of confirmation for the peptide identification, i.e., retention times which are completely absent in the peptide matching by MS/MS ion search. Most proteomics studies consider protein identifications as reliable when two or more peptides are identified and single-hit proteins (only one peptide matched) are discarded. However this "two-peptide" rule has been challenged (Gupta et al., *J. Proteome Res.* 2009, 8, 4173-4181). With the use of the present invention, it is believed that a "one-peptide" rule should be sufficient for protein identification as long as the single peptide can be confirmed with full confidence. Therefore, in cases of protein identification with low coverage or low scores, synthetic peptides should be used for confirmation whenever feasible.

Because the five purified proteins studied in the present Examples were available to the inventors, the same IDA experiments described herein above were run on digested protein standards instead of synthetic peptides. Not surprisingly, the Mascot search identified the appropriate target protein for each of these reference standards and the results for one peptide for each protein are included in Table 1, along with transgenic samples for comparison and confirmation. The peptide scores for the purified protein standards are considerably higher than that for the transgenic leaf samples, as one would expect given the complexity of the un-enriched crude extracts from the transgenic leaf samples.

The XIC of one MRM from the digested recombinant protein standard is shown along with transgenic and null samples in the bottom panes of FIGS. 2-6. For each of the five target proteins, the LC-MRM ion chromatogram of the digested protein standards fully confirms the peptides identified previously by Mascot MS/MS search, including some of the low score peptides, with almost the exact same retention times (±2%). It should be noted that one synthetic peptide, which may be purchased and is often available in just a few days, should suffice when a recombinant protein is not available. Additionally, availability of synthetic peptides makes it possible to further optimize the sensitivity of LC-MRM (both MS compound and source parameters and LC parameters) to study target proteins at even lower expression levels. During the optimization process, only the best product ion, rather than all product ions, is needed, as discussed in the previous section.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A method of detecting a polypeptide of interest in a plant without the use of a reference standard, said method comprising:
   (a) obtaining a plant wherein the expression of said polypeptide of interest is suppressed and a negative control plant that does express said polypeptide of interest;
   (b) preparing a sample from said plant and a negative control sample from said negative control plant for analysis; and
   (c) determining whether an MRM transition signal associated with identified tryptic peptides for the polypeptide of interest is present at a determined retention time in LC-MRM ion chromatograms of said sample and said negative control sample;
   wherein the presence of an MRM transition signal at said determined retention time in said negative control sample, and the absence of a corresponding MRM transition signal in said sample, indicates the absence of said polypeptide of interest in said plant.

2. The method of claim 1, further comprising the steps of:
   (a) producing a synthetic peptide comprising the amino acid sequence of said tryptic peptide associated with said MRM transition signal;
   (b) preparing a synthetic peptide sample from said synthetic peptide for analysis;
   (c) predicting the MRM transitions for said synthetic peptide;
   (d) performing an information-dependent acquisition (IDA) method on said sample using liquid chromatography-tandem mass spectrometry (LC-MS/MS), said IDA method comprising:
      (i) predicting all tryptic peptides that can be derived from said polypeptide of interest and predicting the multiple reaction monitoring (MRM) transitions for each of said tryptic peptides;
      (ii) performing a survey scan of said sample using LC-MS/MS to monitor for the predicted MRM transitions of said tryptic peptides, wherein tandem mass spectrometry is performed in MRM mode, and wherein LC-MRM ion chromatograms are produced for said sample;

(iii) performing an IDA scan when an individual MRM transition signal exceeds a predetermined threshold, wherein said IDA scan is an enhanced product ion (EPI) scan that is performed using tandem mass spectrometry in linear ion trap mode, and wherein said EPI scan produces a set of MS/MS spectra for said tryptic peptide associated with said MRM transition signal; and (iv) identifying said tryptic peptide associated with said MRM transition signal, and determining the retention time of said MRM transition signal in said LC-MRM ion chromatograms, by submitting said set of MS/MS spectra to at least one database;

(d) repeating said IDA method of step (c) with said negative control sample; and (e) comparing said LC-MRM ion chromatograms of said sample, said negative control sample, and said synthetic peptide sample at said determined retention time;

wherein the presence of an MRM transition signal at said determined retention time in said sample and said synthetic peptide sample, and the presence of a corresponding MRM transition signal in said negative control sample, confirms the absence of said polypeptide of interest in said plant.

3. The method of claim 1, further comprising the steps of:
(a) producing a recombinant polypeptide comprising the amino acid sequence of said polypeptide of interest;
(b) preparing a recombinant polypeptide sample from said recombinant polypeptide for analysis, wherein said recombinant polypeptide sample is subjected to trypsin digestion;
(c) performing said IDA method of claim 2 with said recombinant polypeptide sample; and
(d) comparing said LC-MRM ion chromatograms of said sample, said negative control sample, and said recombinant polypeptide sample at said determined retention time;

wherein the presence of an MRM transition signal at said determined retention time in said sample and said synthetic peptide sample, and the presence of a corresponding MRM transition signal in said negative control sample, confirms the absence of said polypeptide of interest in said plant.

4. The method of claim 1, wherein said predicted tryptic peptides have a length of 1 to 30 amino acids or a length of 6 to 20 amino acids.

5. The method of claim 2, wherein said predicted tryptic peptides are within the Q1 range of 300 to 1200 m/z or the Q1 range of 350 to 900 m/z.

6. The method of claim 2, wherein a maximum of 50 MRM transitions are detected by said IDA method.

7. The method of claim 2, wherein said IDA method is performed using a hybrid triple quadrupole mass spectrometer.

8. The method of claim 1, wherein said polypeptide of interest is a transgenic polypeptide.

9. The method of claim 1, wherein said plant is a transgenic plant.

10. The method of claim 1, wherein said plant and said negative control plant are monocots, or said plant and said negative control plant are dicots.

11. The method of claim 10, wherein said monocots are maize, sugarcane, wheat, rice, barley, *sorghum*, or rye, and wherein said dicots are soybean, *Brassica*, sunflower, cotton, or alfalfa.

12. A method of determining the relative expression level of a polypeptide of interest in a plurality of plants without the use of a reference standard, said method comprising:
(a) obtaining a plurality of plants wherein the expression of said polypeptide of interest is suppressed in the plants and a negative control plant that does express said polypeptide of interest;
(b) preparing a first sample from a first plant, a second sample from a second plant, and a negative control sample from said negative control plant, wherein said first sample, said second sample, and said negative control sample are subjected to trypsin digestion;
(c) performing an IDA method on said first sample using LC-MS/MS, said IDA method comprising:
(i) predicting all tryptic peptides that can be derived from said polypeptide of interest and predicting the MRM transitions for each of said tryptic peptides;
(ii) performing a survey scan of said first sample using LC-MS/MS to monitor for the predicted MRM transitions of said tryptic peptides, wherein tandem mass spectrometry is performed in MRM mode, and wherein LC-MRM ion chromatograms are produced for said first sample;
(iii) performing an IDA scan when an individual MRM transition signal exceeds a predetermined threshold, wherein said IDA scan is an EPI scan that is performed using tandem mass spectrometry in linear ion trap mode, and wherein said EPI scan produces a set of MS/MS spectra for said tryptic peptide associated with said MRM transition signal; and
(iv) identifying said tryptic peptide associated with said MRM transition signal, and determining the retention time of said MRM transition signal in said LC-MRM ion chromatograms, by submitting said set of MS/MS spectra to at least one database;
(d) repeating said IDA method of step (c) with said second sample and said negative control sample;
(e) determining whether an MRM transition signal is present at said determined retention time in said LC-MRM ion chromatograms of said first sample, said second sample, and said negative control sample, wherein the absence of an MRM transition signal at said determined retention time in said first sample and said second sample, and the presence of a corresponding MRM transition signal in said negative control sample, indicates the absence of said polypeptide of interest in said plurality of plants;
(f) integrating the peaks associated with said MRM transition signals in said LC-MRM ion chromatograms of said first sample and said second sample; and
(g) determining the relative expression level of said polypeptide of interest in said first plant and said second plant, wherein a higher relative expression level is indicated by a larger integrated peak value.

13. The method of claim 12, further comprising the steps of:
(a) producing a synthetic peptide comprising the amino acid sequence of said tryptic peptide associated with said MRM transition signal;
(b) preparing a synthetic peptide sample from said synthetic peptide for analysis;
(c) predicting the MRM transitions for said synthetic peptide;

(d) performing steps (ii) through (iv) of said IDA method of claim 12 with said synthetic peptide sample; and
(e) comparing said LC-MRM ion chromatograms of said first sample, said second sample, said negative control sample, and said synthetic peptide sample at said determined retention time;
wherein the absence of an MRM transition signal at said determined retention time in said first sample, said second sample, and the presence of a corresponding MRM transition signal in said negative control sample and said synthetic peptide sample, confirms the absence of said polypeptide of interest in said plurality of plants.

14. The method of claim 12, further comprising the steps of:
(a) producing a recombinant polypeptide comprising the amino acid sequence of said polypeptide of interest;
(b) preparing a recombinant polypeptide sample from said recombinant polypeptide for analysis, wherein said recombinant polypeptide sample is subjected to trypsin digestion;
(c) performing said IDA method of claim 12 with said recombinant polypeptide sample; and
(d) comparing said LC-MRM ion chromatograms of said first sample, said second sample, said negative control sample, and said recombinant polypeptide sample at said determined retention time;
wherein the absence of an MRM transition signal at said determined retention time in said first sample, said second sample, and the presence of a corresponding MRM transition signal in said negative control sample and said synthetic peptide sample, confirms the absence of said polypeptide of interest in said plurality of plants.

15. The method of claim 12, wherein the relative expression level of said polypeptide of interest is determined in more than two plants.

16. The method of claim 12, wherein said IDA method is performed using a hybrid triple quadrupole mass spectrometer.

* * * * *